United States Patent [19]

Honda et al.

[11] Patent Number: 5,902,887
[45] Date of Patent: May 11, 1999

[54] PROCESS FOR PRODUCING 3-AMINO-2-OXO-1-HALOGENOPROPANE DERIVATIVES

[75] Inventors: Yutaka Honda; Satoshi Katayama; Kunisuke Izawa; Masakazu Nakazawa; Takayuki Suzuki; Naoko Kanno, all of Kawasaki, Japan

[73] Assignee: Ajinomoto Co., Inc., Tokyo, Japan

[21] Appl. No.: 09/059,370

[22] Filed: Apr. 14, 1998

Related U.S. Application Data

[62] Division of application No. 08/752,169, Nov. 18, 1996, Pat. No. 5,767,316.

[30] Foreign Application Priority Data

Nov. 17, 1995 [JP] Japan ..................................... 7-299827

[51] Int. Cl.$^6$ .................. C07D 307/20; C07C 219/04
[52] U.S. Cl. ........................... 549/475; 560/42; 560/155; 560/170; 560/172
[58] Field of Search .............................. 560/42, 155, 170, 560/172; 549/475

[56] References Cited

U.S. PATENT DOCUMENTS 5,648,511   7/1997   Ng et al. ................................. 558/345
5,767,316   6/1998   Honda et al. ........................... 564/502

*Primary Examiner*—Ba K. Trinh
*Attorney, Agent, or Firm*—Oblon, Spivak, McClelland, Maier & Neustadt, P.C.

[57] ABSTRACT

Compounds formed by reacting a protected amino acid with an alkali metal enolate of an alkyl acetate are reacted with a halogenating agent for halogenation of the 2-position, or a protected amino acid is reacted with an alkali metal enolate of an alkyl halogenoacetate, to form a 4-amino-3-oxo-2-halogenobutanoic acid ester derivative, and hydrolysis and decarboxylation are conducted to produce a 3-amino-2-oxo-1-halogenopropane derivative or its salt. The present method is a useful process for producing a 3-amino-2-oxo-1-halogenopropane derivatives which can easily be converted to a 3-amino-1,2-epoxypropane.

3 Claims, No Drawings

PROCESS FOR PRODUCING 3-AMINO-2-OXO-1-HALOGENOPROPANE DERIVATIVES

This application is a Division of application Ser. No. 08/752,169, filed on Nov. 18, 1996 now U.S. Pat. No. 5,767,316.

BACKGROUND OF THE INVENTION

1. Field of the Invention

The present invention relates to a process for producing 3-amino-2-oxo-1-halogenopropane derivatives which can easily be converted to optically active 3-substituted-3-amino-1,2-epoxypropane derivatives which are equivalents of α-aminoalcohol derivatives that are important as intermediates for HIV protease inhibitors or certain enzyme inhibitors.

2. Discussion of the Background

α-Aminoalcohol derivatives which can easily be converted from optically active 3-substituted-3-amino-1,2-epoxypropane derivatives are used as intermediates for synthesis of a large number of HIV protease inhibitors such as Ro3l-8959 (Parkes K. et al (Roche), *J. Org. Chem.*, 1994, vol. 59, p.3656) SC-52151 (Getman D. P. et. al. (Monsanto), *J. Med. Chem.*, 1993, vol. 36, p. 288) VX478 (Verte, WO9405639), and AG1343 (Lilly, WO9521164].

Known examples of a method of producing 3-amino-1,2-epoxypropane derivatives include a method in which the 2-position of an N-protected-3-amino-2-oxo-1-halogenopropane is reduced stereoselectively to form the corresponding alcohol, and this alcohol is then epoxidized through dehydrohalogenation (Getman D. P. et al., *J. Med. Chem.*, 1993, vol. 36, p. 288), a method in which N-protected-3-amino-1-propene is epoxidized oxidatively asymmetrically (Luly J. R. et al., J. Org. Chem., 1987, vol. 52, p. 1487), and a method in which methylene is inserted into N-protected-3-amino-1-propanal (Searle G. D., WO93/23388.).

In the first method, it is important how the key intermediate N-protected 3-amino-2-oxo-1-halogenopropane or its equivalent substance can be produced industrially at low cost. However, industrialization of this method is limited since it has to use diazomethane having quite a high explosiveness and a strong toxicity as a sub-starting material (see for example, Getman D. P. et al., *J. Med. Chem.*, 1993, vol. 36, p. 288; Okada Y. et al., *Chem. Pharm. Bull.*, 1988, vol. 36, p. 4794; EP 346867; and Raddatz P. et al.,*J. Med. Chem.*, 1991, vol. 34, p. 3267). Further, there is a method in which an N-substituted amino acid ester is reacted with a halomethyl anion. However, quite an unstable halomethyl anion is used, and a halogen to be introduced into the 1-position is presumably limited to chlorine or fluorine in view of a common chemical knowledge. For these reasons, industrialization of this method is limited (Barluenga et al.,*J. Chem. Soc., Chem. Commun.*, 1994).

Still further, a method in which, after a C-terminus of an N-substituted amino acid is activated, the resulting compound is reacted with fluoromalonic acid half ester for decarboxylation (EP 442754) can be mentioned as a known technology. In this method, however, the halogen is limited to a specific element, fluorine. Therefore, this method cannot be applied to a system containing chlorine or bromine for achieving the object of the present invention.

In the second method, the Wittig reaction of a costly aldehyde (3-amino-1-propanal) is utilized to produce the key intermediate, N-substituted-3-amino-1-propene. Consequently, this method involves quite a high cost. Further, in the third method, not only does the method of forming the intermediate N-substituted aldehyde entail a high cost, but also carbene has to be formed at a low temperature when inserting methylene. Accordingly, this method is not industrially appropriate.

Thus, there remains a need for a method of preparing compounds which can easily be converted to intermediates useful for preparing HIV proteases. There also remains a need for a need for processes for preparing amino-2-oxo-1-halogenopropane derivatives and 3-amino-1,2-epoxypropane derivatives.

SUMMARY OF THE INVENTION

Accordingly, it is one object of the present invention to provide a novel process for preparing compounds which can be easily converted into α-aminoalcohol derivatives.

It is another object of the present invention to provide a novel process for preparing compounds which can easily be converted into 3-amino-1,2-epoxypropane derivatives.

It is another object of the present invention to provide a novel process for preparing 3-amino-1,2-epoxypropane derivatives.

It is another object of the present invention to provide a novel process for preparing 3-amino-2-oxo-1-halogenopropane derivatives.

It is another object of the present invention to provide an industrial process for producing a 3-amino-2-oxo-1-halogenopropane derivative which can easily be converted to a 3-amino-1,2-epoxypropane derivative.

It is another object of the present invention to provide novel intermediates useful for preparing such 3-amino-2-oxo-1-halogenopropane derivatives.

These and other objects, which will become apparent during the following detailed description, have been achieved by the inventors' discovery that a 3-amino-1,2-epoxypropane derivative or its equivalent substance can be produced from the corresponding 3-amino-2-oxo-1-halogenopropane in a high yield. The inventors have also discovered its precursor, a novel α-halogeno-β-keto ester derivative and a process for producing the same.

Thus, the present invention provides a process for producing a 3-amino-2-oxo-1-halogenopropane derivative represented by formula (V)

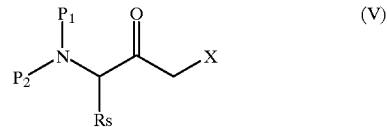

wherein:

$R_s$ represents hydrogen, an optionally substituted alkyl group having from 1 to 10 carbon atoms, an optionally substituted aryl group having from 6 to 15 carbon atoms, an optionally substituted aralkyl group having from 7 to 20 carbon atoms, or the above-mentioned groups containing a hetero atom in the carbon skeleton; $P_1$ and $P_2$, independently from each other, represent hydrogen or an amino-protecting group, or $P_1$ and $P_2$ together form a difunctional amino-protecting group, and at least one of $P_1$ and $P_2$ is not hydrogen; and X represents a halogen atom other than fluorine; or its salt, which comprises:

(i) reacting a compound represented by formula (I)

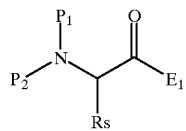
(I)

5 wherein $R_s$, $P_1$, and $P_2$ and X are as defined above; and $E_1$ represents, as an active carboxy terminus, an alkoxy ester residue having from 1 to 10 carbon atoms, a phenoxy or benzyloxy group which may have a substituent on the ring, an active ester residue of N-oxysuccinimide or 1-oxybenzotriazole, an active thioester residue, an imidazolyl group or a residue capable of forming an acid halide, an acid anhydride or an acid azido, with an alkali metal enolate of an acetate, to obtain a compound represented by formula (II)

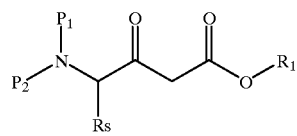
(II)

wherein $R_s$, $P_1$ and $P_2$ are as defined above, and $R_1$ represents an optionally substituted alkyl group having from 1 to 10 carbon atoms, an optionally substituted aryl group having from 6 to 15 carbon atoms, an optionally substituted aralkyl group having from 7 to 20 carbon atoms, a trialkylsilyl group having from 4 to 10 carbon atoms, a phenyldialkylsilyl group having 8 to 10 carbon atoms or a diphenylalkylsilyl group having 13 to 15 carbon atoms;

(ii) reacting the compound of formula (II) with a halogenating agent for halogenation of the 2-position to form a 4-amino-3-oxo-2-halogenobutanoic acid ester derivative represented by formula (III)

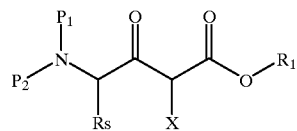
(III)

wherein $R_s$, $P_1$, $P_2$, X, and $R_1$ are as defined above;

(iii) further hydrolyzing the resulting compound of formula (III), to obtain a hydrolyzate; and (iv) decarboxylating the hydrolyzate, to obtain the compound of formula (V).

The present invention also provides a process for producing a 3-amino-2-oxo-1-halogenopropane derivative represented by formula (V)

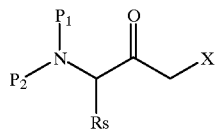
(V)

wherein $R_s$, $P_1$, $P_2$, and X are as defined above, or its salt, which comprises:

(i) reacting a compound represented by formula (I)

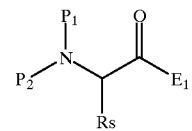
(I)

wherein $R_s$, $P_1$, $P_2$, and $E_1$ are as defined above, with an alkali metal enolate or dianion of a compound represented by formula (IV)

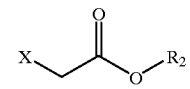
(IV)

wherein X is as defined above, and $R_2$ represents hydrogen, an optionally substituted alkyl group having from 1 to 10 carbon atoms, an optionally substituted aryl group having from 6 to 15 carbon atoms, an optionally substituted aralkyl group having from 7 to 20 carbon atoms, a trialkylsilyl group having from 3 to 10 carbon atoms, a phenyldialkylsilyl group having 8 to 10 carbon atoms or a diphenylalkylsilyl group having 13 to 15 carbon atoms, to form the 4-amino-3-oxo-2-halogenobutanoic acid ester or salt derivative represented by formula (III')

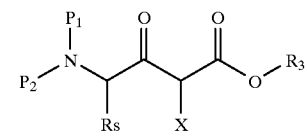
(III')

wherein $R_s$, $P_1$, $P_2$, and X are as defined above, and $R_3$ represents an alkali metal, an optionally substituted alkyl group having from 1 to 10 carbon atoms, an optionally substituted aryl group having from 6 to 15 carbon atoms, an optionally substituted aralkyl group having from 7 to 20 carbon atoms, a trialkylsilyl group having from 3 to 10 carbon atoms, a phenyldialkylsilyl group having 8 to 10 carbon atoms, or a diphenylalkylsilyl group having 13 to 15 carbon atoms; and (ii) further hydrolyzing the resulting compound of formula (III), to obtain a hydrolyzate; and (iii) decarboxylating the hydrolyzate, to obtain the compound of formula (V).

The present invention also provides the 4-amino-3-oxo-2-halogenobutanoic acid ester or salt derivative of formula (III') or its salt which is an intermediate for the production of the compound of formula (V).

DETAILED DESCRIPTION OF THE PREFERRED EMBODIMENTS

The compound of formula (I) which is used in the present invention is a natural or artificial protected α-amino acid in which an amino group is protected with a protecting group and a carboxyl group is converted to a functional group which can be reacted with a nucleophilic agent.

The compound of formula (I) has an optical activity owing to the stearic configuration of the carbon atom at the root of an amino acid. For example, when an optically active amino acid is selected as a starting material, it can easily be used in the synthesis of the desired compound having an optical activity. Thus, when $R_s$ is not hydrogen, the configuration at the carbon bearing $R_s$ can be either S or R or a mixture thereof. In a preferred embodiment, the configuration of the carbon bearing $R_s$ is the same as that in the α-carbon of a natural α-amino acid.

$R_s$ in formula (I) is hydrogen or an ordinary substituent such as alkyl, aryl or aralkyl. For example, when it is a methyl group, a compound having an alanine-like structure is formed. When it is a benzyl group, a compound having a phenylalanine-like structure is formed. $P_1$ and $P_2$ are ordinary amino-protecting groups. Either $P_1$ or $P_2$ may be a hydrogen atom, or $P_1$ and $P_2$ together form a difunctional amino-protecting group. Examples thereof include benzyloxycarbonyl, tert-butoxycarbonyl, acetyl, formyl, benzoyl, dibenzyl, and phthaloyl. $P_1$ and $P_2$ may be selected in consideration of the selectivity for the functional group in the hydrolysis and the decarboxylation of the ester group ($R_1$) which will be described later. $E_1$ is a functional group of a carboxy terminal which can be reacted with a nucleophilic agent. Examples thereof include lower ester residues, active ester residues, acid halide residues and acid anhydride residues. Examples thereof include methoxy, ethoxy, benzoxy, substituted benzoxy, phenoxy, substituted phenoxy, N-oxysuccinimide, 1-oxybenzotriazole, imidazolyl, chlorine, bromine, methoxycarboxy, isobutoxycarboxy and tert-butylcarboxy.

Specific examples of the compound of formula (I) include N-benzyloxycarbonyl-L-phenylalanine methyl ester, N-benzyloxycarbonyl-L-phenylalanine-N-oxysuccinimide ester, N,N-dibenzyl-L-phenylalanine-p-nitrophenyl ester and N-benzyloxycarbonyl-S-phenyl-L-cysteine methyl ester.

The compound of formula (I) can be formed by protecting an amino group of a natural or artificial a-amino acid by a method which is ordinarily used in synthesis of a peptide, and then esterifying or halogenating the carboxyl group by a method which is ordinarily used in synthesis of a peptide.

The conversion of the compound of formula (I) to the compound of formula (II) is a reaction in which the ester, the acid halide or the acid anhydride of formula (I) is reacted with an acetate enolate derived from an acetic acid ester to form the β-keto ester. The acetate enolate refers to an alkali metal salt, and a lithium salt is most-preferable. This enolate is formed by adding an acetic acid ester to a solution of a base such as lithium amide, lithium diisopropylamide or lithium tert-butoxide. The ester of the acetic acid ester refers to a carboxylic acid ester which is ordinarily used. Examples thereof include an alkyl ester, an aralkyl ester and a silyl ester. Specifically, a hydrolyzable ester of methyl, ethyl, tert-butyl, benzyl or triethylsilyl is available.

The acetate enolate has to be used in an amount of at least 1 equivalent based on the substrate (I). Since 1 equivalent of the base is used to form the β-keto ester enolate of the product, the reaction proceeds well when at least 2 equivalents of the acetate enolate is used.

This reaction rapidly proceeds at a temperature of from −100° C. to room temperature. The optimum temperature varies depending on the compound. Typically, the reaction is completed at a temperature of from −75° C. to −30° C. for from 5 to 60 minutes. Suitable reaction solvents to be used include hydrocarbons or ethers. Specific examples of the reaction solvent include tetrahydrofuran, hexane, toluene and a mixture thereof. The reaction concentration is not particularly limited, and it may be determined depending on the solubility of the reaction product.

After the completion of the reaction, the reaction solution is treated with an acid to protonate the alkali metal salt of the product and give the β-keto ester of formula (II). This compound can easily be purified through silica-gel chromatography. However, the compound in an unpurified state can also be used as a starting material in the subsequent reaction.

The conversion from the compound of formula (II) to the compound of formula (III) is a reaction in which a hydrogen of the active methylene in the β-keto ester of formula (II) is oxidatively halogenated with various halogenating agents to obtain the 4-amino-3-oxo-2-halogenobutanoic acid ester derivative of formula (III). The reaction easily proceeds only by mixing the β-keto ester with the halogenating agent in a solvent.

The halogenating agent may be N-bromosuccinimide, copper (II) bromide or bromine in the case of bromination, and N-chlorosuccinimide, copper (II) chloride, sulfuryl chloride or chlorine in the case of chlorination. The halogenating agent has to be used in an amount of a theoretical equivalent or more based on the β-keto ester of formula (II). When the amount is set exactly at the theoretical equivalent in order to prevent side reactions, the most preferable yield can be provided in many cases. The theoretical equivalent refers to an amount which is required from the chemical equation. For example, the amount of N-bromosuccinimide is 1 equivalent based on the β-keto ester, and that of copper (II) bromide is 2 equivalents.

The reaction conditions strongly depend on the structure of the reaction product or the reagents, and have to be determined depending on the compounds. For example, when $R_s$ is benzyl, $P_1$ is benzyloxycarbonyl, $P_2$ is hydrogen, $R_1$ is tert-butyl and N-bromosuccinimide is used as a reagent, the reaction is conducted at a temperature of from −20° C. to room temperature for from 10 to 60 minutes. The reaction solvent includes halogen solvents such as methylene chloride and chloroform, ethyl acetate, ether and toluene. The reaction concentration is not particularly limited, and may be determined depending on the solubility of the reaction product.

The reaction product can be purified through recrystallization or the like as required. However, the reaction product in the unpurified state can be used as a starting material in the subsequent reaction. A diastereomer is formed depending on the selectivity during the halogenation. It can be separated through thin-layer chromatography or silica-gel column chromatography. However, this separation is not required in view of the purpose of the process in the present invention.

The compound of formula (III), it's trimethylsilyl ester and it's acid salt which are the compound of formula (III') can also be obtained by reacting the compound of formula (I) with a halogenoacetate enolate or a dianion of halogenoacetic acid. That is, as stated above, when forming the compound of formula (III'), the desired compound can be obtained in one step by using a chlorcacetic acid ester, a chloroacetic acid, a bromoacetic acid ester or a bromoacetic acid of formula (VI) instead of an acetic acid ester used in the method that undergoes formation of the compound of formula (II).

In this react-on, when an enolate which is prepared from trimethylsilyl halogenoacetate or the dianion which is prepared from halogenoacetic acid are used, a product of formula (III') ($R_s$ is trimethylsilyl or alkaline metal) can be converted to a compound of formula (V) with decarboxylation by treating an acid solution in one step.

The halogenoacetate enolate can be formed by a method in which an enolate is formed by the method that undergoes formation of the compound of formula (II). The conditions under which this enolate is reacted with the compound of formula (I) are the same as the above-mentioned conditions.

Since the stability of the halogenoacetate enolate is inferior to that of the acetate enolate, the reaction has to be conducted at a low temperature of −60° C. or less.

It may be selected as required whether the compound of formula (III') is converted from the compound of formula (I)

directly or through formation of the compound of formula (II), because the yield varies with the identity of the substituents or the protecting groups of the compound of formula (I).

The compound of formula (III') is a novel compound which is an intermediate that is important in the present invention. The structure of this compound may be viewed as containing the corresponding enol substance as a convertible isomer. As the convertible isomer, for example, a 4-amino-3-oxo-2-halogenobutanoic acid ester derivative represented by formula (VIII) can be mentioned.

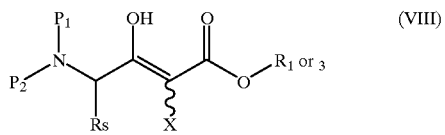

wherein $R_s$ represents a hydrogen, an optionally substituted alkyl group having from 1 to 10 carbon atoms, an optionally substituted aryl group having from 6 to 15 carbon atoms, an optionally substituted aralkyl group having from 7 to 20 carbon atoms, or the above-mentioned groups containing a hetero atom (such as O or N) in the carbon skeleton; $P_1$ and $P_2$, independently from each other, represent hydrogen or an amino-protecting group, or $P_1$ and $P_2$ together form a difunctional amino-protecting group, and at least one of $P_1$ and $P_2$ is not hydrogen; and $R_{1 \text{ or } 3}$ represents an alkali metal an optionally substituted alkyl group having from 1 to 10 carbon atoms, an optionally substituted aryl group having from 6 to 15 carbon atoms, an optionally substituted aralkyl group having from 7 to 20 carbon atoms, a trialkylsilyl group having from 3 to 10 carbon atoms, a phenyldialkylsilyl group having 8 to 10 carbon atoms or a diphenylalkylsilyl group having 13 to 15 carbon atoms.

The compound of formula (III) or (III') is converted to the compound of formula (V) by hydrolyzing the 4-amino-3-oxo-2-halogenobutanoic acid ester derivative, and decarboxylating the hydrolyzate at the same time.

The hydrolysis may be conducted by a method which is conventionally employed in organic chemistry. Examples of such a hydrolysis include alkali hydrolysis of a lower alkyl ester, acid hydrolysis of a tertiary alkyl ester, catalytic hydrogenation of a benzyl ester and hydrolysis of a silyl ester under weakly acidic to neutral conditions. However, it is required that the halogen introduced under such hydrolysis conditions is not influenced. The optimum conditions vary with the structure of the compound. The hydrolysis using a system of a tertiary alkyl ester or a silyl ester gives good results in many cases.

The desired product can be extracted and isolated from the reaction solution to the organic solvent and can be purified with silica-gel chromatography, recrystallization, or the like.

The typical reaction conditions are that when $R_1$ is tert-butyl, the reaction is conducted in a formic acid solution for from a few hours to scores of hours at room temperature. The reaction time can be decreased to from a few minutes to 1 hour by increasing the reaction temperature. The reaction concentration is not particularly limited and may be determined depending on the solubility of the reaction product.

The 3-amino-2-oxo-1-halogenopropane derivative of formula (V) obtained by these methods is, as described in the literature (see for example, Getman D. P. et al., *J. Med. Chem.*, 1993, vol. 36, p. 288; Okada Y. et al., *Chem. Pharm. Bull.*, 1988, vol. 36, p. 4794; EP 346867; and Raddatz P. et al., *J. Med. Chem.*, 1991, vol. 34, p. 3267), a known compound which is useful as an intermediate for the synthesis of a HIV protease inhibitor. It is known that the above-mentioned compound is formed into an intermediate of a more advanced form by undergoing an existing reaction in two stages as schematically shown below (Getman D. P. et al., *J. Med. Chem.*, 1993, vol. 36, p. 288).

That is, it is possible that the 3-amino-2-oxo-1-halogenopropane derivative of formula (V) having a halogenomethyl ketone skeleton is converted into a halohydrin represented by formula (VI) through a reductive reaction of a carbonyl group

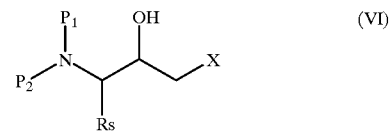

wherein $R_s$, $P_1$, $P_2$, and X are as defined above and this compound is further easily epoxidized under alkaline conditions to form a compound of formula (VII)

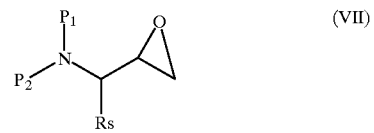

wherein $R_s$, $P_1$, and $P_2$ are as defined above.

In the above-mentioned reductive reaction of the carbonyl group, the binding stearic configuration of the substituent indicated by $R_s$ in the 3-position can be subjected to the stereoselective reduction. It can be achieved using a common reducing agent typified by sodium borohydride. For example, when a compound in which $R_s$ is a benzyl group, the stearic configuration in the 3-position is the S-configuration, and an urethane-type protecting group is selected as an amino-protecting group, is reduced with sodium borohydride, the stearic configuration of at the carbon bearing the resulting hydroxyl group is preferentially the S-configuration in a ratio of from 2:1 to 20:1, and purification can be conducted through recrystallization. Further, the resulting alcohol is converted to a (2S, 3S) epoxy compound which is important as an intermediate for a HIV protease inhibitor.

In the above-given descriptions of the compounds of formulae (I)–(VII), the substituents $R_s$, $R_1$, $R_2$, $R_3$, and $E_1$ are defined in terms of optionally substituted alkyl groups, optionally substituted aryl groups, optionally substituted aralkyl groups, and phenoxy or benzyloxy groups with -substituted rings. Suitable substituents for these groups include, halogen, such as F, Cl, Br, and I; nitrogen-containing substituents, such as —NO$_2$, —NH$_2$, —NHR, —NRR', and —N$_3$; sulfur-containing substituents, such as —SH, —SR, —S(O)R, and —S(O)$_2$R; phosphorus-containing substituents, such as —PRR' and —P(O)RR'; and oxygen-containing substituents, such as —OH, —OR, —OCOR, and —COOR (wherein R and R' are alkyl groups, e.g. $C_{1-4}$ alkyl groups).

The conversion of the starting compound of formula (I) to the desired compound of formula (V) and the epoxy compound of formula (VII) is schematically shown below.

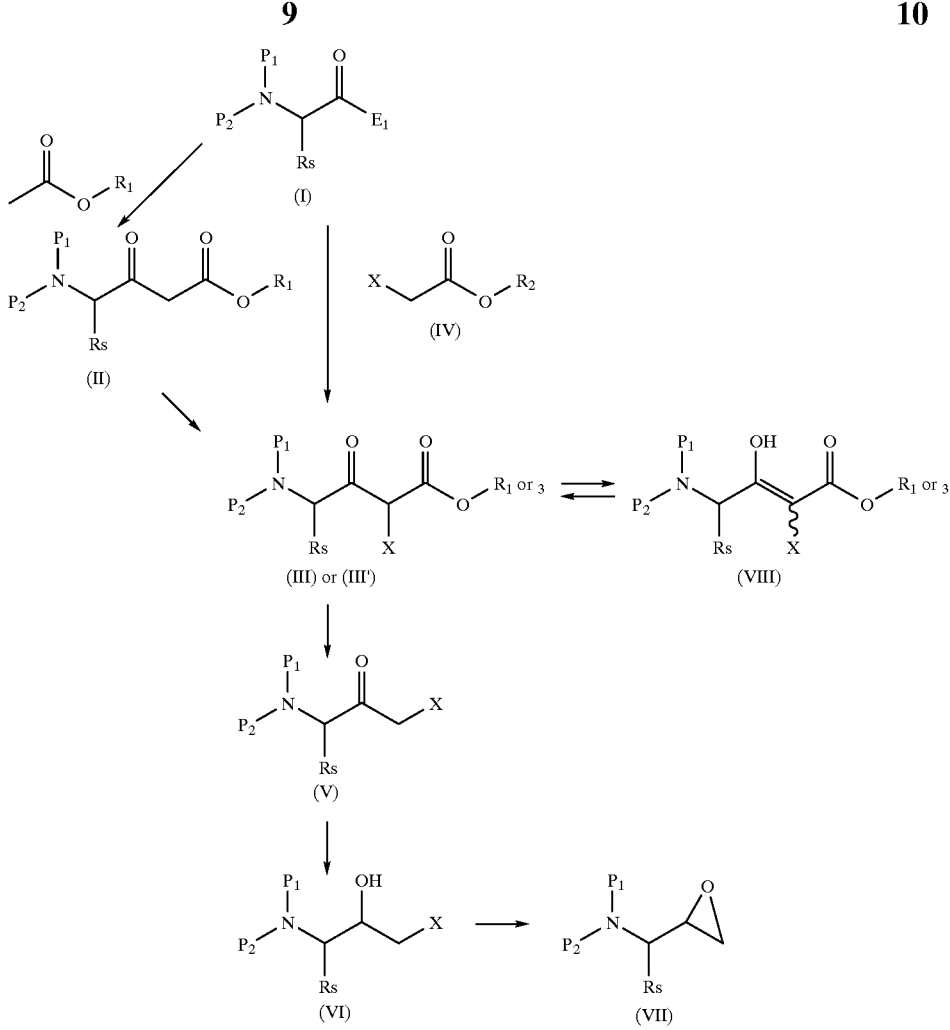

wherein $R_s$, $R_1$, $R_2$, $R_3$, $E_1$, X, $P_1$, and $P_2$ are as defined.

EXAMPLES

The present invention is illustrated more specifically by referring to the following Examples. However, the present invention is not limited thereto. The temperature is given in centigrade unless otherwise specified. Unless otherwise indicated, all "%" values are "%" by weight, and all solvent ratios are by volume. Proton nuclear magnetic resonance (NMR) spectra were recorded on a Varian 300 MHz spectrometer. Chemical shifts (δ) are given in ppm. The abbreviations used in Examples are as follows.

Boc: tert-butoxycarhonyl
Z: benzyloxycarbonyl
THF: tetrahydrofuran
LDA: lithium diisopropylamide
NCS: N-chlorosuccinimide
NBS: N-bromosuccinimide

Production Example 1

Production of N, N-dibenzyl-L-phenylalanine benzyl ester (Ia)

Twenty-five grams (151.3 mmol) of (L)-phenylalanine and 66.67 g (482.4 mmol) of potassium carbonate were dissolved in 100 ml of water, and 57.51 g (454.3 mmol) of benzyl chloride were added thereto. The mixture was heat-stirred at 95° C. for 19 hours. After the reaction mixture was cooled to room temperature, 67 ml of n-heptane and 50 ml of water were added thereto. The organic layer was washed twice with 50 ml of a mixture of methanol and water at a volume ratio of 1:2 and was then dried over anhydrous sodium sulfate. The dried substance was filtered and concentrated to give 61.64 g (90%, 121.8 mmol) of the above-mentioned compound (Ia) in a yield of 84.7%.

$^1$H-NMR(300 MHz, CDCl$_3$) δ:3.00 (dd,1H), 3.14(dd,1H), 3.53(d,2H), 3.71(t,1H), 3.92(d,2H), 5.12(d,1H), 5.23(d,1H), 6.99–7.40(m,20H) Mass spectrum (FAB) 436(MH+)

Production Example 2

Production of N,N-dibenzyl-L-phenylalanine p-nitropohenyl ester (Ib)

N,N-dibenzyl-L-phenylalanine hydrochloride (7.64 g, 20.0 mmol) was added to 50 ml of chloroform, and 20.0 ml of 10% aqueous ammonia were added dropwise to the suspension for neutralization. The organic layer was separated, washed with 20 ml of water, then dried over magnesium sulfate, and filtered. The filtrate was concentrated, the resulting residue was dissolved in 50 ml of chloroform, and 2.89 g (20.4 mmol) of p-nitrophenol and 4.13 g (20.0 mmol) of N,N'-dicyclohexylcarbodiimide were added to the solution in this order while being cooled with ice. The mixture was reacted overnight. To the reaction solution were added 30 ml of ethyl acetate, and the N,N'-dicyclohexylurea which precipitated was removed by filtration. The filtrate was washed with a 10% potassium carbonate aqueous solution. The organic layer was separated, and concentrated. The resulting residue was redissolved in 30 ml of ethyl acetate, and the insoluble materials which precipitated were removed by filtration. The filtrate was concentrated, and the resulting crude product was purified through silica-gel column chromatography to obtain 7.77 g (16.65 mmol) of the above-mentioned compound (Ib).

$^1$HNMR(300 MHz, CDCl$_3$) δ:3.13 (dd, J=7.4,13.7 Hz,1H) 3.26(dd, J=8.2,13.9 Hz,1H), 3.72(d,J=14.0 Hz,2H), 3.96(dd,J=7.4,8.2 Hz,1H), 4.06(d,J=14.0 Hz,2H), 7.14(d,J=9.2 Hz,2H), 7.06–7.37(m,15H), 8.26(d,J=9.3 Hz,2H) Mass spectrum (FAB) 467(MH+)

Example 1

Production of (4S) -4-(N,N-dibenzylamino)-4-benzyl-3-oxobutanoic acid tert-butyl ester (IIa)

A solution (2.0 M) (24 ml, 48 mmol) of LDA in heptane, THF and ethyl benzene was dissolved in 64 ml of anhydrous THF, and the mixed solution was cooled to −53° C. in an argon atmosphere. To this solution was added dropwise a solution of 5.8 g (50 mmols) of tert-butyl acetate in 12 ml of THF for approximately 15 minutes while maintaining the temperature at from −45° C. to −50° C. After the completion of the dropwise addition, the mixture was stirred at −53° C. for 1 hour. Subsequently, a solution of 7.2 g (15 mmols, purity 90%) of N,N-dibenzyl-L-phenylalanine benzyl ester (Ia) in 8 ml of THF was added dropwise thereto for approximately 15 minutes while maintaining the temperature at from −48° C. to −52° C. After the completion of the dropwise addition, the reaction temperature was raised to −5° C. After three hours, a solution of 16.5 g of citric acid in 50 ml of water was added to the reaction solution to stop the reaction. The resulting mixture was extracted twice with ethyl acetate (100 ml and 50 ml), and the organic layer was washed with 20 ml of 10% citric acid, with 10 ml of a saturated aqueous solution of sodium chloride, with 5% sodium hydrogencarbonate aqueous solution (20 ml×4) and with 10 ml of a saturated aqueous solution of sodium chloride in this order. The organic layer was dried over anhydrous magnesium sulfate, and the filtrate was concentrated. The concentrate was purified through silica-gel column chromatography (eluent—mixture of n-hexane and ethyl acetate at a ratio of 4:1) to give 6.09 g (13.7 mmol) of the above-mentioned compound (IIa).

$^1$HNMR(300 MHz, CDCl$_3$) δ: 1.25(s,9H), 2.93(dd,J=3.9, 13.5 Hz,1H), 3.20(dd,J=9.0,13.5 Hz,1H), 3.40(d,J=15.6 GHz,2H), 3.55(m,2H), 3.62(dd,J=3.9,9.0 Hz,1H), 3.82(d,J=13.5 Hz,2H), 7.10–7.38 (m,15H) Mass spectrum (FA-B) 444(MH+)

Example 2

Production of (4S)-4-(N benzyloxycarbonyl)amino-4-benzyl-3-oxobutanoic acid tert-butyl ester (IIb)

A solution (2.0 M)(14 ml, 28 mmol) of LDA in heptane, THF and ethyl benzene was dissolved in 30 ml of anhydrous THF in an argon atmosphere, and the mixed solution was cooled to −45° C. To this solution was added dropwise a solution of 3.7 g (32 mmol) of tert-butyl acetate in 4 ml of THF for approximately 15 minutes while maintaining the temperature at from −40° C. to −45° C. After the completion of the dropwise addition, the resulting solution was stirred at −50° C. for 30 minutes, and a solution of 2.5 g (8 mmol) of N-benzyloxycarbonyl-L-phenylalanine methyl ester (Ic) was added dropwise thereto for approximately 10 minutes while maintaining the temperature at from −40° C. to −45° C. After the completion of the dropwise addition, the reaction solution was stirred at −40° C. for 30 minutes, then heated to 0° C. and stirred for 20 minutes. Forty milliliters of a 20% citric acid aqueous solution were added to the reaction solution to stop the reaction. The mixture was extracted with ethyl acetate (50 ml×2), and the organic layer was washed with 5 ml of water, with 20 ml of a 5% sodium hydrogencarbonate aqueous solution and with 10 ml of water in this order. The resulting organic layer was dried over anhydrous magnesium sulfate, and the filtrate was concentrated. The concentrate was purified through silica-gel column chromatography (eluent—mixture of n-hexane and ethyl acetate at a ratio of 4:1) to give 3.08 g (7.77 mmol) of the above-mentioned compound (IIb).

$^1$HNMR(300 MHz, CDCl$_3$) δ: 1.44 (s,9H), 2.99 (dd,J=7.1,14.1 Hz,1H), 3.17(dd,J=6.1,14.1 Hz,1H), 3.38(m,2H), 4.68(bq,J=approx. 7,1H), 5.07(s,2H), 5.38(bd,J=7.9 Hz,1H), 7.12–7.35(m,10H)

$^{13}$CNMR(75 MHz, CDCl$_3$) δ: 28.0, 37.1, 48.2, 60.7, 67.0, 82.4, 127.1, 128.1, 128.2, 128.5, 128.7, 129.2, 135.8, 137.9, 165.8, 182.0, 201.7 Mass spectrum (FAB) 398(MH+)

Example 3

Production of (4S)-4-(N-benzyloxycarbonyl)amino-4-benzyl-3-oxobutanoic acid ethyl ester (IIc)

A solution (2.0 M) (4 ml, mmol) of LDA in heptane, THF and ethyl benzene was dissolved in 8 ml of anhydrous THF in an argon atmosphere, and the mixed solution was cooled to −50° C. To this solution was added dropwise a solution of 740 mg (8 mmol) of ethyl acetate in 2 ml of THF for approximately 5 minutes while maintaining the temperature at from −50° C. to −45° C. After the completion of the dropwise addition, the mixture was stirred at −50° C. for 30 minutes, and a solution of 626 mg (2 mmol) of N-benzyloxycarbonyl-L-phenylalanine methyl ester (Ic) in 2 ml of THF was further added to the above-mentioned solution for approximately 5 minutes while maintaining the temperature at from −50° C. to −45° C. After the completion of the dropwise addition, the reaction solution was stirred at −50° C. for 30 minutes, the temperature was then raised to room temperature, and the mixture was stirred for 5 minutes. Ten milliliters of a 10% citric acid aqueous solution was added to the reaction solution to stop the reaction. The reaction mixture was extracted with ethyl acetate. The organic layer was passed through a silica-gel column, and then concentrated to give 826 mg of the above-mentioned compound (IIc) as a crude oil.

$^1$HNMR(300 MHz, CDCl$_3$) δ: 1.22–1.30 (m,3H), 2.92–3.05 (m,1H), 3.05–3.22(m,1H), 3.40–3.54(m,2H), 4.10–4.19(m,2H), 4.66(m,1H), 5.07(bs,2H), 5,55(bd,J=7.8 Hz,1H), 7.11–7.38(m,10H)

Example 4

Production of (4S)-4-(N-tert-butoxycarbonyl)amino-4-benzyl-3-oxobutanoic acid tert-butyl ester (IId)

A solution (2.0 M)( 27 ml, 54 mmol) of LDA in heptane, THF and ethyl benzene was dissolved in 50 ml of anhydrous THF in an argon atmosphere, and the mixed solution was cooled to −45° C. To this solution was added dropwise a solution of 7.0 g (60 mmols) of tert-butyl acetate in 5 ml of THF for approximately 20 minutes while maintaining the temperature at from −40° C. to −45° C. After the completion of the dropwise addition, the mixture was stirred at −50° C. for 30 minutes. To this solution was added dropwise a solution of 4.18 g (15 mmols) of N-tert-butoxycarbonyl-L-phenylalanine methyl ester (Id) in 5 ml of THF for approximately 20 minutes while maintaining the temperature of from −40° C. to −45° C. After the completion of the dropwise addition, the reaction solution was stirred at −50°

C. for 30 minutes, and 40 ml of a 25% citric acid aqueous solution were added to the reaction solution to stop the reaction. After the organic solvent in the reaction solution was distilled off under reduced pressure, the residue was extracted with 100 ml of ethyl acetate, and the organic layer was washed with 20 ml of water. This organic layer was concentrated and passed through a silica-gel column (eluent:mixture of n-hexane and ethyl acetate at a volume ratio of 4:1) to give 5.92 g of crystals. The NMR analysis of the crystals revealed the above-mentioned compound (IId) containing 15% of the unreacted starting compound (Id).

$^1$HNMR(300 MHz, CDCl$_3$) δ: 1.39(s,9H), 1.46(s,9H), 2.96(dd,J=7.4,14.0 Hz,1H), 3.16(dd,J=5.7,14.0 HZ,1H), 3.34–3.45(m,2H), 4.57(bq,J=approx.6. Hz,1H), 5.09(bd,J=7.7 Hz,1H), 7.11–7.30 (m,5H)

$^{13}$CNMR(75 MHz, CDCl$_3$) δ: 27.8, 28.2, 36.9, 48.0, 60.4, 80.0, 82.0, 126.9, 128.4, 129.2, 136.2, 155.1, 166.0, 202.2

Example 5

Production of (4S) -4-(N,N-dibenzylamino)-4-benzyl-3-oxo-2-bromobutanoic acid tert-butyl ester (IIIA)

(1) Finely divided copper (II) bromide (0.45 g, 2.0 mmol) was dissolved in 2 ml of ethyl acetate. A solution obtained by dissolving 0.44 g (1.0 mmol) of the compound (IIa) obtained in Example 1 and 0.14 ml (1.0 mmol) of triethylamine in 2 ml of ethyl acetate was added thereto at 25° C. while being stirred. After the reaction was conducted at 25° C. for 36 hours in an argon atmosphere, 5 milliliters of a 5% citric acid aqueous solution were added to the mixture to separate the organic layer. This organic layer was concentrated to give 0.45 g (0.86 mmol) of an isomer mixture of the above-mentioned compound (IIIA) as brown crystals.

$^1$HNMR (300 MHz, CDCl$_3$) (isomer mixture) δ: 0.90 (s,9/2H), 1.44(s,9/2H), 2.99(dd,J=3.7,13.5 Hz,1H), 3.14–3.29(m,1H), 3.50(dd,J=5.6,13.3 Hz,2H), 3.83(dd,J=10.3,13.3 Hz,2H), 3.82(dd,1/2H), 4.03(dd,3.7,9.5,1/2H), 5.42(s,1/2H), 5.51(s,1/2H), 7.14–7.34(m, 15H) Mass spectrum (ESI) 522.3, 524.3(MH+)

(2) The compound (IIa) (0.89 g, 2.0 mmols) obtained in Example 1 was dissolved in 10 ml of diethyl ether. NBS (0.39 g, 2.0 mmol) was added thereto while being stirred with ice cooling, and the mixture was further stirred for 2 hours. After the reaction was further conducted at room temperature for 13 hours, 5 ml of water were added to the reaction mixture to separate the organic layer. The organic layer was concentrated to give 1.23 g of brown crystals. The NMR analysis of the crystals revealed that approximately 35% of the starting compound (IIa) still remained and the main product was an isomer mixture of the above-mentioned compound (IIIa).

Example 6

Production of (4S) -4-(N-benzyloxycarbonyl)amino-4-benzyl-3-oxo-2-chlorobutanoic acid tert-butyl ester (IIIb)

The compound (IIb) (0.8 g, 2.0 mmols) obtained in Example 2 was dissolved in 5 ml of chloroform. NCS (264 mg, 1.98 mmol) was added thereto while being stirred with ice cooling, and the mixture was further stirred for 3 hours while being cooled with ice. Two milliliters of water were added to the reaction solution to separate the organic layer. This organic layer was concentrated to give 912 mg of crystals. One hundred milligrams of a part of the crystals were eluted through silica-gel thin-layer chromatography (eluent: mixture of n-hexane and ethyl acetate at a ratio of 4:1) to give 40 mg of an isomer mixture of the abovementioned compound (IIIb).

$^1$HNMR(300 MHz, CDCl$_3$) (isomer mixture) δ 1.45–1.48 (m,9H), 2.95–3.05 (m,1H), 3.18–3.38(m,1H), 4.85–5.10(m, 4H), 5.20–5.3 5(m,1H), 7.14–7.35(m,10H)

Example 7

Production of (4S)-4-(N-benzyloxycarbonyl)amino-4-benzyl-3-oxo-2-bromobutanoic acid tert-butyl ester (IIIc)

The compound (IIb) (0.8 g, 2.0 mmol) obtained in Example 2 was dissolved in 5 ml of chloroform. NBS (338 mg, 1.9 mmols) was added thereto while being stirred with ice cooling, and the mixture was further stirred for 30 minutes while being cooled with ice. Three milliliters of water were added to the reaction solution to separate the organic layer. This organic layer was concentrated to give 921 mg of an isomer mixture of the above-mentioned compound (IIIC) as crude light brown crystals.

$^1$HNMR(300 MHz, CDCl$_3$) (isomer mixture) δ 1.43–1.50 (m,9H), 3.00(dd,J=7.4,14.1 Hz,$_1$H), 3.21(dd,J=5.7,14.1 Hz,1H), 4.82–5.03(m,1H), 4.89(bs,1H), 5.07(bs,2H), 5.20 (bd,J=6.0 Hz,1H), 7.17–7.35(m,10H) Mass spectrum (FAB) 476,478(MH+)

Example 8

Production of (3S)-3-(N,N-dibenzyl)amino-3-benzyl-2-oxo-1-bromopropane (Va)

The compound (IIIA) (41 mg, 0.078 mmols) obtained in Example 5 was dissolved in 4 N hydrogen chloride (ethyl acetate solution, 1 ml) The mixture was stirred at room temperature for 13 hours for reaction. Three milliliters of ethyl acetate were added to the reaction solution, and were neutralized with a saturated aqueous solution of sodium hydrogencarbonate. The organic layer was concentrated to give 30 mg of the above-mentioned crude compound (Va).

$^1$HNMR(300 MHz, CDCl$_3$) δ: 3.00(dd,J=3.9,13.5 Hz,1H), 3.25 (dd,J=9.0,13.5, Hz,1H), 3.55(d,J=15.6 Hz,2H), 3.67(dd,J=3.9,9.0 Hz,1H), 3.84(d,J=15.6 Hz,2H), 4.42(s, 1H),4.48(s,1H), 7.10–7.38(m,15H)

Example 9

Production of (2S)-3-(N-benzyloxycarbonyl)amino-3-benzyl-2-oxo-1-chloropropane (Vb)

The compound (IIb) (3S g, 88 mmol) obtained in Example 2 was dissolved in 88 ml of methylene chloride. Sulfuryl chloride (7.23 ml, 90 mmol) was added thereto while being stirred with ice cooling. The mixture was stirred for 1 hour while being cooled with ice and further at room temperature for 30 minutes. The reaction solution was concentrated to give 37 g of the crude compound (IIIB) as crystals. The crystals (35 g) were suspended in 80 ml of formic acid (purity 90%). The suspension was heated at 80° C. while being stirred, and was reacted for 30 minutes. The reaction solution was cooled, and formic acid was distilled off under reduced pressure to obtain the above-mentioned compound (Vb) as crystals. Further, the crystals were recrystallized from 200 ml of isopropanol, and were dried to give 19.55 g of the above-mentioned compound (Vb).

$^1$H-NMR(300 MHz, CDCl$_3$) δ: 3.05 (dd, J=7.2,14.0 Hz,1H) 3.25(dd,J=7.1,14.0, Hz,1H), 3.97(d,J=16.2 Hz,1H), 4.14(d,J=16.2 Hz,1H), 4.77(q,J=4.77 Hz,2H), 5.08(s,2H), 5.29(d,J=7.2 Hz,1H),7.12–7.35 (m,10H)

$^{13}$C-NMR(75 MHz, CDCl$_3$) δ:37.8, 47.4, 58.7, 67.3, 127.5, 128.1, 128.3, 128.6, 129.0, 129.1, 135.2, 135.9, 155.7, 201.0

Example 10

Production of (3S)-3-(N-benzyloxycarbonylamino)-3-benzyl-2-oxo-1-bromopropane (Vc)

(1) The compound (IIIC) (56 mg, 0.12 mmol) obtained in Example 7 was dissolved in 1 ml of methylene chloride, and 0.3 ml of trifluoroacetic acid were added thereto. The mixture was stirred at 60° C. for 17 hours for reaction. The reaction solution was neutralized with a saturated aqueous solution of sodium hydrogencarbonate, and was extracted with ethyl acetate. The organic layer was concentrated, and then eluted through silica-gel thin-layer chromatography (eluent:mixture of n-hexane and ethyl acetate at a ratio of 4:1) to give 20 mg of the above-mentioned compound (Vc).

$^1$HNMR, (300 MHz, CDCl$_3$) δ: 3.06(dd,J=7.2,13.9 Hz,1H) 3.09(dd,J=6.9,13.9 Hz,1H), 3.81(d,J=13.7 Hz,1H), 3.93(d,J=13.7 Hz,1H), 4.82(bq,J=7.3 Hz,1H), 4.89(bs,1H), 5.08(bs,2H), 5.34(bd,J=7.2 Hz,1H), 7.13–7.39(m,10H)

$^{13}$CNMR(75 MHz, CDCl$_3$) δ: 33.1, 37.7, 58.8, 67.2, 127.3, 128.0, 128.3, 128.5, 128.9, 129.1, 135.5, 136.0, 155.8, 200.4 Mass spectrum (ESI) 376(MH+)

(2) The compound (IIIC) (360 mg, 0.756 mmol) was dissolved 2 ml of formic acid, and the solution was stirred at 25° C. for 15 hours for reaction. After formic acid was distilled off under reduced pressure, the concentrate was neutralized with a 5% sodium hydrogencarbonate aqueous solution, and was extracted with ethyl acetate. The organic layer was concentrated to give 296 mg of the compound (Vc) as crude crystals. Further, the crystals were eluted through silica-gel thin-layer chromatography (eluent:mixture of n-hexane and ethyl acetate at a ratio of 4:1) to give 149 g of the purified crystals of the above-mentioned compound (Vc).

Example 11

Production of (3S) -3-(N-benzyloxycarbonyl)amino-3-benzyl-2-hydroxy-1-chloropropane (VIb)

The compound (Vb) (136 mg, 0.4 mmol) obtained in Example 9 was dissolved in 1.5 ml of methanol. To this solution were added 17 mg (0.44 mmols) of sodium borohydride at 0° C., and the mixture was stirred at 0° C. for 2 hours for reaction. To the reaction solution was added 1 N hydrochloric acid to stop the reaction. Then, methanol was distilled off under reduced pressure. This solution was extracted with ethyl acetate, and the organic layer was concentrated to give 138 mg of the mixture of the above-mentioned compounds (2S, 3S)-(VIb) and (2R, 3S)-(VIb) at a ratio of 74:26 as light yellow crystals.

$^1$HNMR(300 MHz, CDCl$_3$) (diastereomer mixture) δ: 2.93(dd,J=8.4,14.0 Hz,1H), 3.00(dd,J=4.9,14.0 Hz,1H), 3.50–3.60(m,1H), 3.65(dd,J=4.2,12.0 Hz,1H), 3.81–3.89(m,1H),3.92–4.03 (m,1H), 4.87(bd,J=approx.8 Hz,1H), 5.03 (bs,2H), 7.17–7.37(m,10H)

Example 12

Production of (3S)-3-(N-benzyloxycarbonyl)amino-3-benzyl-2-hydroxy-1-bromopropane (VIc)

The compound (Vc) (142 mg, 0.37 mmol) obtained in Example 10 was dissolved in a mixed solvent containing 3 ml of methanol and 1 ml of THF. To this solution were added 16 mg (0.41 mmol) of sodium borohydride at 0° C., and the mixture was stirred at from 0° C. to 5° C. for 2 hours. To the reaction solution were added 2 ml of 1 N hydrochloric acid to stop the reaction. Then, methanol and THF were distilled off under reduced pressure. The thus-obtained slurry was extracted with ethyl acetate, and the organic layer was concentrated to give 146 mg of the mixture of the above-mentioned compounds (2S, 3S)-(VIc) and (2R, 3S)-(VIc) at a ratio of 84:16 as light yellow crystals.

$^1$HNMR(300 MHz, CDCl$_3$) (diastereomer mixture) δ: 2.90(dd,J=9.7,14.0 Hz,1H), 2.99(dd,J=4.7,14.0 Hz,1H), 3.38–3.47 (m,1H), 3.53(dd,J=3.6,10.6 Hz,1H), 3.81–3.90 (m,1H), 3.93–4.03(m,1H), 4.86(bd,J=approx.8 Hz,1H), 5.03 (s,2H), 7.16–7.35(m,10H)

Example 13

Production of (3S)-3-(N-benzyloxycarbonyl)amino-3-benzyl-1,2-epoxypropane (VIIb)

(1) One hundred milligrams (0.3 mmol) of the mixture of the compounds (2S,3S)-(VIb) and (2R, 3S)-(VIc) (at a ratio of approximately 3:1) obtained in Example 11 were dissolved in 2 ml of THF. To this solution were added 40 mg (0.27 mmol) of potassium tert-butoxide at –10° C., and the mixture was stirred at –10° C. for 15 minutes for reaction. The reaction solution io was extracted with 3 ml of water and with 10 ml of methylene chloride to separate the organic layer. This organic layer was concentrated. The resulting crystals were purified through silica-gel thin-layer chromatography (mixture of n-hexane and ethyl acetate at a ratio of 2:1) to give 20 mg of the mixture of the above-mentioned compounds (2S, 3S)-(VIIb) and (2R, 3S)-(VIIb) (at a ratio of approximately 3:1).

$^1$HNMR(300 MHz, CDCl$_3$) (diastereomer mixture) δ: 2.52–2.58(m,2/4H,(2R,3S)), 2.71–2.80(m,6/4H,(2S,3S)), 2.83–2.95 (m,1H), 2.99(dd,J=5.0,14.2 Hz,1H), 3.69–3.72 (m,1H,3/4H,(2S,3S)), 4.12.–4.25(m,1H,1/4H,(2R,3S)), 4.67–4.80(m,1H), 5.03(s,6/4H, (2S,3S)), 5.05(s,2/4H,(2R, 3S)), 7.18–7.35 (m,10H)

(2) The mixture (164 mg) of the compounds (2S, 3S)-(VIc) and (2R, 3S)-(VIc) (at a ratio of approximately 5:1) obtained in Example 12 was dissolved in 4.5 ml of methanol. To this solution were added 58 mg (0.41 mmols) of potassium carbonate at room temperature, and the mixture was further stirred at room temperature for 1 hour for reaction. The reaction solution was extracted with 3 ml of 1N hydrochloric acid and with 10 ml of ethyl acetate to separate the organic layer. This organic layer was concentrated. The resulting crystals were purified through silica-gel thin-layer chromatography (mixture of n-hexane and ethyl acetate at a ratio of 2:1) to give 79 mg of the mixture of the above-mentioned compounds (2S, 3S)-(VIIb) and (2R, 3S)-(VIIb) (at a ratio of approximately 5:1) as white crystals.

Example 14

Production of (4S)-4-(N,N-dibenzyl)amino-4-benzyl-3-oxo-2-chlorobutanoic acid tert-butyl ester (IIId)

Anhydrous THF (3.2 ml) was mixed with 2.0 M (0.39 ml, 0.78 mmol) of a solution of LDA in heptane, THF and ethyl benzene in an argon atmosphere, and the mixture was cooled to –70° C. To this solution were added dropwise 0.13 ml (0.85 mmol) of tert-butyl chloroacetate (IVa). After the mixture was stirred, for 30 minutes, a solution of 154 mg (0.34 mmol) of the compound (Ib) in 1.0 ml of anhydrous THF was added thereto dropwise. While the temperature was gradually raised, the mixture was stirred for 3 hours. After this, the reaction solution was heated to room temperature, 3.0 mg of a 10% citric acid aqueous solution and 10 ml of ethyl acetate were added thereto in this order to extract the reaction mixture. The organic layer was washed with 10 ml of water, dried over magnesium sulfate, and filtered. The filtrate was concentrated, and the resulting crude product was purified through silica-gel thin-layer chromatography to give 200.2 mg of the mixture of the above-mentioned compounds (2S, 4S)-(IIID) and (2R, 4S)-(IIID). The diastereomer ratio was approximately 2:1 as calculated from the $^1$H-NMR integration ratio.

$^1$HNMR (300 MHz, CDCl$_3$) (diastereomer mixture) δ: 0.86 (s,6H), 1.44(s,3H), 2.94–3.04(m,1H), 3.17(dd,J=9.8, 13.4 Hz,1/3H), 3.26(dd,J=9.8,13.3 Hz,2/3H), 3.50(d,J=13.2 Hz,4/3H), 3.51(d,J=13.2 Hz,2/3H), 3.81(d,J=13.2 Hz,4/3H), 3.85(d,J=13.1 Hz,2/3H), 3.87(dd,J=3.0,9.7 Hz,2/3H), 4.00 (dd,J=3.0,9.7 Hz,1/3H), 5.37(s,1/3H), 5.48(s,2/3H), 7.08–7.39(m,15H) Mass spectrum (FAB) 478(MH+)

Example 15

Production of (4S)-4-(N-benzyloxycarbonyl)amino-4-benzyl-3-oxo-butanoic acid tert-butyl ester (IIb)

A solution (2.M) (231 ml, 462 mmol) of LDA in heptane, THF and ethylbenzene was dissolved in 400 ml of anhydrous THF in argon atmosphere, and the mixed solution was cooled to −50° C. To this solution was added dropwise a solution of 58.1 g (500 mmol) of tert-butyl acetate in 40 ml of THF for approximately 40 minutes while maintaining the temperature at −45° C. to −50° C. After the completion of the dropwise addition, the mixture was stirred at −45° C. for 30 minutes. To this solution was added dropwise a solution of 39.4 g (125 mmol) of N-benzyloxycarbonyl-L-phenylalanine methyl ester (Ic) in 40 ml of THF for approximately 30 minutes while maintaining the temperature at −45° C to −50° C. After the completion of the dropwise addition, the reaction solution was stirred at −45° C. for 1 hour, and 500 ml of 2 N hydrochloric acid and 150 g of ice were added to the reaction solution to stop the reaction. The temperature was then raised to room temperature, and the organic layer was separated. The water layer was extracted with 350 ml of toluene, and the organic layers were combined. The organic layer was washed with 50 ml of 5% sodium hydrogencarbonate aqueous solution and 50 ml of 25% sodium chloride aqueous solution in that order. The organic layer was dried over anhydrous magnesium sulfate, and the filtrate was concentrated to give 58.1 g (86.4 wt %, 126 mmol) of the above-mentioned crude compound.

Example 16

Production of (4S)-(N-benzyloxycarbonyl)amino-4-benzyl-3-oxo-2-chlorobutanoic acid tert-butyl ester (IIIb)

40.5 (86.4 wt %, 88 mmol) of (4S)-4-(N-benzyloxycarbonyl)amino-4-benzyl-3-oxo-butanoic acid tertbutyl ester (IIb) was dissolved in 88 ml of dichloromethane. 7.23 ml (90 mmol) of sulfuryl chloride was added thereto while being stirred with ice cooling, and the mixture was further stirred for 1 hour with ice cooling and for 30 minutes at room temperature. The reaction mixture was concentrated under reduced pressure below 300C to give 48.6 g of the above-mentioned crude compound as crystals. 2 g of the crude product was recrystallized from 10 ml of toluene to give the purified crystals. (main isomer)

$^1$H-NMR (300 MHz, CDCl$_3$) δ: 1.44(s,9H), 2.99(dd,J=7.5,14.1 Hz,1H), 3.20(dd,J=6.1,14.1 Hz,1H), 4.85(s,1H), 4.97(br.q,J=8.4 Hz,1H), 5.60(s,2H), 5.25(br.d,J=8.4 Hz,1H), 7.1–7.3S(m,10H)

$^{13}$C-NMR (75 MHz, CDCl$_3$) δ: 27.5, 37.7, 59.5, 60.0, 67.2, 85.0, 127.3, 128.1, 128.3, 128.5, 128.9, 129.2, 135.3, 136.0, 155.6, 163.1, 197.4 mass spectrum (FAB) 432 (MH+) 454(MNa+)

Example 17

Production of (3S)-(N-benzyloxycarbonyl)amino-3-benzyl-2-oxo-1-chloropropane (Vb)

46.6 g of crude crystals of (4S)-4-(N-benzyloxycarbonyl) amino-4-benzyl-3-oxo-2-chlorobutanoic acid tert-butyl ester (IIIB) obtained in Example 16 was suspended in 80 ml of formic acid (90%), and the mixture was stirred for 20 minutes at 80° C. This reaction mixture was concentrated under reduced pressure to give the above-mentioned compound as crude crystals.

The crude crystals were dissolved in 200 ml of 2-propanol at 60° C., and cooled to 5° C. The resulting crystals were collected by filtration and washed with 50 ml of 2-propanol. The crystals obtained were dried under reduced pressure to give 20.1 g (60 mmol) of the above-mentioned compound.

Example 18

Production of (2S,3S)-3-(N-benzyloxycarbonyl)amino-3-benzyl-2-hydroxy-1-chloropropane (VIb)

17.0 g (51.2 mmol) of (3S)-3-(N-benzyloxycarbonyl) amino-3-benzyl-2-oxo-1-chloropronane (Vb) was dissolved in a mixed solvent containing 180 ml of dichloromethane and 180 ml of methanol. 2.03 g (53.8 mmol) of sodium borohydride was added portionwise thereto at 0° C. for 10 minutes, and the mixture was further stirred for 30 minutes at 0° C. 12.9 ml (226 mmol) of acetic acid was added to the reaction mixture, and the mixture was concentrated under reduced pressure to remove methanol. 50 ml of water was added thereto, and the resulting mixture was extracted twice with dichloromethane (150 ml and 50 ml). The combined organic layer was concentrated to give the mixture of above-mentioned compound and the diastereomer ((2R,3S)-form) (at ratio of approximately 84:16) as white crystals.

1 g of these crystals was recrystallized from 15 ml of a mixed solvent containing ethyl acetate and hexane (at a ratio of 5:1) to give 0.6 g (97% d.e.) of the above-mentioned compound.

((2S, 3S) -form)

$^1$H-NMR (300 MHz, CDCl$_3$) δ: 2.87(dd,J=9.0,14.1 Hz,1H), 3.00(dd,J=4.6,14.1 Hz,1H), 3.55(dd,J=7.3,11.3 Hz,1H), 3.60(br.s,1H), 3.62 (dd,J=4.3,11.3 Hz,1H), 3.86 (br.q, J=approx 5 Hz, 1H), 3.96–4.06(m,1H), 5.01(s,2H), 5.31(br.d,J=approx. 8.5 Hz,1H), 7.18–7.33 (m,10H)

$^{13}$C-NMR (75 MHz, CDCl$_3$) δ:35.3, 47.1, 54.6, 66.5, 73.2, 126.4, 127.8, 127.9, 128.3, 128.3, 129.3, 136.3, 137.5, 156.0 mass spectrum (ESI) 334.2 (MH+) 356.2 (MNa+) 689.3 (2MNa+)

Example 19

Production of (2S-3S)-3-(N-benzyloxycarbonyl)amino-3-benzyl-1,2-epoxypropane (VIIb)

The crude diastereomeric mixture of 3-(N-benzyloxycarbonyl)amino-3-benzyl-2-hydroxy-1-chloropropane (VIb) obtained in Example 18 ((2S,3S)-(VIb) and (2R,3S)-(VIb) at a ratio of 84:16) was dissolved in 600 ml of methanol. To this solution was added 14.1 g (102 mmol) of potassium carbonate at room temperature, and the mixture was further stirred at room temperature for 3 hours for reaction. After the insoluble matter of the reaction mixture was removed by filtration and washed with 20 ml of methanol, the filtrate was concentrated to approximately 100 ml under reduced pressure below 35° C. The resulting mixture was acidified with 100 ml of 0.5 N hydrochloric acid, and was extracted twice with dichloromethane (150 ml and 150 ml). The organic layer was concentrated under 40° C. to give 14.0 g (47.1 mmol) of the mixture of the above-mentioned compound and its diastereomer (2R,3S)-(VIIb) (at a ratio of 84:16) as white crystals.

The crystals obtained was recrystallized from 6 ml of a mixed solvent containing ethyl acetate and hexane (at a ratio of 1:1) to give 0.58 g (97% de) of the above-mentioned compound.

((2S,3S) -form)

$^1$H-NMR (300 MHz, CDCl$_3$) δ: 2.71–2.80(m,2H), 2.85 (dd,J=8.1,14.1 Hz,1H), 2.91(dd,J=2.7,6.4 Hz,1H), 2.98(dd, J=S.1,14.1 Hz,1H), 3.68–3.82(m,1H), 4.77(br.d,J=5.9 Hz,1H), 5.03(s,2H), 7.17–7.33(m,10H)

$^{13}$C-NMR (75 MHz, CDCl$_3$) δ: 37.5, 46.7, 53.0, 53.2, 66.8, 126.8, 128.0, 128.1, 128.5, 128.6, 129.3, 136.2, 136.4, 155.7 Mass spectrum (ESI) 298.2(MH+), 320.2(MNa+), 336.3 (MK$^+$), 617.5 (2MNa$^+$).

Example 20

Production of (2R3S)-3-(N-benzyloxycarbonyl)amino-2-hydroxy-1-(N-isobutyl)amino-4-phenylbutane (IXa)

4.47 g (15.0 mmol) of the diastereomeric mixture of 3(N-benzyloxycarbonyl)amino-3-benzyl-1,2-epoxypropane (VIIb) obtained in Example 19 ((2S, 3S)-(VIIb) and (2R, 3S)-(VIIb) at a ratio of 84:16) was suspended in 29 ml of ethanol. To this suspension was added 22.4 ml (225 mmol) of isobutylamine, and the mixture was stirred at 70° C. for 1 hour for reaction. The reaction solution was concentrated to give the mixture of the above-mentioned compound and its diastereomer (2S,3S)-(VIIIa) (at a ratio of 84:16) as white crystals.

The titled compound (2R,3S)-(VIIIa) was prepared substantially in accordance with the above-mentioned procedure, using the (2S,3S)-(VIIb).
(2R, 3S)-form)
$^1$H-NMR (300 MHz, CDCl$_3$) δ: 0.90 (d, J=6.6 Hz, 6H), 1.60–1.80 (m,1H), 2.38 (d,J=6.8 Hz, 2H), 2.65 (dd, J=6.8, 12.4 Hz,1H), 2.70 (dd, J=4.0, 12.4 Hz, 1H), 2.70 (br.s,1H), 2.86 (dd, J=8.1, 14.1 Hz, 1H), 2.99 (dd, J=4.8, 14.1 Hz, 1H), 3.49 (br.q, J=approx 4.5 Hz, 1H), 3.80–3.95 (m, 1H), 5.02 (s, 2H), 5.11 (br.d, J=9.0 Hz, 1H), 7.19–7.32 (m, 10H)
$^{13}$C-NMR (75 MHz, CDCl$_3$) δ: 20.5, 28.3, 36.6, 51.4, 55.0, 57.9, 66.5, 70.4, 126.4, 127.8, 128.0, 128.4, 128.4, 129.5, 136.6, 137.7, 156.3 Mass spectrum (ESI) 371.2 (MH$^+$)

Example 21

Production of 4-Nitro-N-((2'R (syn),3'S)-3-(N-benzyloxycarbonyl)amino-2'-hydroxy-4'-phenylbutyl)-N-isobutylbenzenesulfonamide (IXb)

6.08 g (15.0 mmol) the diastereomeric mixture of 3-(N-benzyloxycarbonyl)amino-2-hydroxy-1-(N-isobutyl)amino-4-phenylbutane (IXa) obtained in Example 20 ((2R, 3S)-(IXa) and (2S,3S)-(IXa) at a ratio of 84:16) was dissolved in 40 ml of dichloromethane. To this solution were added 2.55 g (24.1 mmol) of sodium carbonate in 20 ml of water, and 4.0 g (18.0 mmol) of 4-nitrobenzenesulfonylchloride in 5 ml of dichloromethane was added dropwise thereto with ice cooling over 10 minutes. After the reaction mixture was further stirred for 3 hours, the organic layer was separated. The resulting organic layer was concentrated to give the mixture of the above-mentioned compound and its diastereomer (2'S,3'S)-(VIIIb) (at a ratio of 84:16) as white crystals.

These crude crystals were dissolved in 100 ml of ethanol at 70° C. After the crystallization was started at 55° C., it was kept at 55° C. for 1 hour and then was cooled to 20° C. The resulting crystals were collected by filtration and washed with 30 ml of ethanol. The crystals obtained were dried under reduced pressure to give 6.07 g (10.9 mmol) of the above-mentioned compound. ((2'R(syn),3'S)-form)
$^1$H-NMR (300 MHz, CDCl$_3$) δ: 0.84 (d, J=6.1 Hz, 3H), 0.86 (d, J=6.3 Hz, 3H), 1.75–1.95 (m, 1H), 2.88 (dd, J=7.5 14.1 Hz, 2H), 2.96 (d, J=6.8 Hz, 2H), 3.00 (dd, J=4.7, 14.1, 1H), 2.90 (br. s, 1H), 3.12–3.26 (m, 2H), 3.80–3.91 (m, 2H), 4.99 (br. d, J=8.7 Hz, 1H) 5.01 (s, 2H), 7.21–7.32 (m, 10H), 7.92 (d, J=8.7 Hz, 2H), 8.29 (d, J=8.7 Hz, 2H)
$^{13}$C-NMR, (75 MHz, CDCl$_3$) δ: 19.8, 19.9, 35.5, 52.4, 57.7, 66.9, 72.1, 124.3, 26.7, 127.8, 128.2, 128.5, 128.5, 128.6, 129.3, 136.1, 137.2, 144.6, 150.0, 156.5

Example 22

Production of 4-Nitro-N-((2'R (syn), 3'S)-3'-(N-tert--butyloxycarbonyl)amino-2'-hydroxy-4'-phenylbutyl)-N-isobutyl-benzenesufonamide (IXc)

13.0 g (23.4 mmol, 96% de) of 4-nitro-N-((2'R, (syn), 3'S)-3'-(N-benzyloxycarbonyl)amino-2'-hydroxy-4'-phenylbutyl)-N-isobutyl-benzenesulfonamide (IXb) was dissolved in 77 ml of dichloromethane and 2 ml (46.8 mmol) of methanol. To this solution was added 19.3 ml (HBr 93.6 mmol) of 30% hydrobromic acid in acetic acid solution, and the mixture was further stirred at room temperature for 3 hours. The reaction solution was neutralized with 300 ml of 10% sodium carbonate aqueous solution. The resulting mixture was extracted with 100 ml of dichloromethane to separate the organic layer. To this organic layer was added 5.62 g (25.7 mmol) of di-tertbutyl dicarbonate as dissolved in 50 ml of dichloromethane, and the mixture was stirred at room temperature for 2 hours. The reaction solution was concentrated to approximately 100 ml. To the resulting solution were added 100 ml of methanol and 3.23 g (23.4 mmol) of potassium carbonate, and the mixture was further stirred at room temperature for 3 hours to remove the acetylated compound of (VIIIC) at the 2-position. To the resulting mixture was added 1.34 ml (23.4 mmol) of acetic acid to stop the reaction, and the mixture was concentrated. 50 ml of water and 200 ml of dichloromethane were added to the mixture to separate the organic layer. The organic layer was concentrated to give the crude crystals of the above-mentioned compound.

These crude crystals was dissolved in 550 ml of ethanol at 55° C. After the crystallization was started at 40° C., it was cooled to 5° C. The resulting crystals were collected by filtration and washed with 100 ml of ethanol. The crystals obtained were dried under reduced pressure to give 8.71 g (16.7 mmol, 100% de) of the above-mentioned compound as white crystals.
((2'R(syn),3'S)-form)
$^1$H-NMR (300 MHz, CDCl$_2$) δ: 0.87 (d, J=6.6 Hz, 3H), 0.88 (d, J=6. 6 Hz, 3H), 1.36 (s, 9H), 1.81–1.96 (m, 1H), 2.83–2.96 (m, 2H), 2.99 (d, J=7.5 Hz, 2H), 3.20 (d, J=5.3 Hz,2H), 3.70–3.85 (m, 2H), 3.82 (br.s, 1H), 4.64 (br.d, J=7.6 Hz, 1H), 7.21–7.33 (m, 10H), 7.96 (d, J=8.8 Hz, 2H), 8.33 (d, J=8.8 Hz, 2H)
$^{13}$C-NMR (75 MHz, CDCl$_3$) δ: 19.8, 20.0, 26.9, 28.2, 35.6, 52.5, 55.2, 57.5, 72.2, 80.1, 124.3, 126.6, 128.5, 128.6, 129.4, 137.5, 144.8, 150.0, 156.3 Mass spectrum (ESI) 522.3 (MH$^+$), 544.5 (MNa$^+$), 560.4 (MK$^+$)

Example 23

Production of N-(S)-tetrahydrofuran-3-yloxycarbonyl-L-phenylalanine methyl ester (Ie)

0.881 g (10 mmol) of (S)-3-hydroxytetrahydrofuran was dissolved in 10 ml of dichloromethane. To this solution was added 1.34 g (4.5 mmol) of triphosgene, and this solution was cooled to −40° C. 1.04 ml (13.5 mmol) of pyridine dissolved in 5 ml of dichloromethane was added dropwise thereto over approximately 15 minutes, and the mixture was further stirred at room temperature for 3.5 hours. To the resulting solution was added dropwise 1.94 g (9 mmol) of L-phenylalanine methyl ester hydrogen chloride dissolved in 5 ml of dichloromethane with ice cooling. And then 2.12 g (20 mmol) of sodium carbonate dissolved in 20 ml of water was added dropwise thereto over approximately 15 minutes, and the mixture was further stirred at room temperature for 2.5 hours. The organic layer was separated, and was washed with 1 N hydrochloric acid (10 ml×2) and water (10 ml×1). The resulting organic layer was concentrated to give 2.10 g (7.2 mmol) of the above-mentioned compound as a yellow oil.
$^1$H-NMR (300 MHz, CDCl$_3$) δ: 1.96–2.15 (M, 2H), 3. 05 (dd, J=5.6, 13.9 Hz, 1H), 3.13 (dd, J=6.4, 13.9 Hz, 1H), 3.72 (s, 3H), 3.75–3.91 (m, 4H), 4.62 (br.q, J=approx. 6 Hz, 1H), 5.19–5.23 (m,1H), 5.26 (br.q, J=8.7 Hz, 1H), 7.10–7.29 (m, 5H).
$^{13}$C-NMR (75 MHz, CDCl$_3$) δ: 32.7, 38.2, 52.3, 54.7, 66.9, 73.2, 75.5, 127.1, 128.6, 129.2, 135.7, 155.3, 172.0 Mass spectrum (FAB) 294 (MH$^+$)

Example 24

Production of (4S)-4-(N-(S)-tetrahydrofuran-3'-yloxycarbonyl)amino-5-phenyl-3-oxo-pentanoic acid tert-butyl ester (IIe)

A solution 2.0M) (9 ml, 18 mmol) of LDA in heptane, THF and ethylbenzene was dissolved in 20 ml of anhydrous THF under an argon atmosphere, and the mixed solution was cooled to −50° C. To this solution was added dropwise a solution of 2.3 g (20 mmol) of tert-butyl acetate in 3 ml of THF over approximately 10 minutes while maintaining the temperature at −45° C. to −50° C. After the completion of the dropwise addition, the mixture was stirred at −45° C. for 30 minutes. To this solution was added dropwise a solution of 1.75 g (5.3 mmol) of N-(S)-tetrahydrofuran-3-yloxycarbonyl-L-phenylalanine methyl ester (Ie) in 3 ml of THF over approximately 10 minutes while maintaining the temperature at −40° C. to −45° C. After the completion of the dropwise addition, the reaction solution was stirred at −45° C. for 1 hour, and 2.3 ml of acetic acid was added to the reaction solution to stop the reaction. To this were added 20 ml of water and 50 ml of toluene, and the organic layer was separated. The resulting organic layer was washed with 10 ml of 5% sodium hydrogencarbonate aqueous solution and 10 ml of water in that order. The organic layer was dried over anhydrous magnesium sulfate, and the filtrate was concentrated to give 1.95 g (52 mmol) of the above-mentioned crude compound.

$^1$H-NMR (300 MHz, CDCl$_3$) δ: 1.46 (s, 9H), 1.96–2.17 (m, 2H), 2.97 (dd, J=7.3, 14.2 Hz, 1H), 3.17 (dd, J=6.2, 14.2 Hz, 1H), 3.39 (br.s, 2H), 3.70–3.90 (m, 4H), 4.66 (br.q, J=approx. 6.5 Hz, 1H), 5.15–5.23 (m, 1H), 5.34 (br.d, J=7.8 Hz, 1H), 7.15–7.31 (m, SH).

$^{13}$C-NMR (75 MHz, CDCl$_3$) δ: 27.9, 32.7, 37.1, 48.2, 60.6, 66.9, 73.2, 75.6, 82.3, 127.1, 128.7, 129.2, 135.7, 155.4, 165.8, 201.6

Example 25

Production of (4S)-4-(N-(S)-tetrahydrofuran-3'-yloxycarbonyl)amino-2-chloro-5-phenyl-3-oxo-pentanoic acid tert-butyl ester (IIIe)

1.8 g (4.7 mmol) of (4S)-4-(N-(S)-tetrahydrofuran-3'-yloxycarbonyl)amino-5-phenyl-3-oxo-pentanoic acid tert-butyl ester (IIIe) was dissolved in 5 ml of dichloromethane. 0.39 ml (4.7 mmol) of sulfuryl chloride was added thereto while being stirred with ice cooling, and the mixture was further stirred for 1 hour at room temperature. The reaction mixture was concentrated under reduced pressure below 30° C. to give the above-mentioned crude compound.

$^1$H-NMR (300 MHz, CDCl$_3$) δ: 1.40 (s, 9H), 1.96–2.17 (m, 2H), 2.92–3.02 (m, 1H), 3.17–3.25 (m, 1H), 3.67–3.90 (m, 4H), 4.90 (d, J=13.5 Hz, 1H), 4.98 (br.q, J=approx. 6.0 Hz, 1H), 5.15–5.19 (m, 1H), 5.27 (br.d, J=8.3 Hz, 1H), 7.18–7.30 (m, 5H)

$^{13}$C-NMR (75 MHz, CDCl$_3$) δ: 27.7, 32.7, 37.6, 59.1, 60.9, 66.9, 73.0, 75.9, 84.8, 127.3, 128.8, 129.3, 135.3, 155.3, 163.3, 197.4

Example 26

Production of (3S)-1-chloro-2-oxo-3-(N-(S)-tetrahydrofuran-3'-yloxycarbonyl)amino-4-phenylbutane (Vd)

The crude compound of (4S)-4-(N-(S)-tetrahydrofuran-3'-yloxycarbonyl)amino-2-chloro-5-phenyl-3-oxo-pentanoic acid tert-butyl ester (IIIe) obtained in Example 25 was dissolved in 5 ml of formic acid (90%), and the mixture was stirred for 15 minutes at 80° C. This reaction mixture was concentrated under reduced pressure, and to the resulting mixture was added 10 ml of 2-propanol to form crystals. The crystals were dissolved at 60° C., and the mixture was stirred at room temperature for 2 hours and at 5° C. for 30 minutes. The resulting crystals were collected by filtration and were washed with 2 ml of 2-propanol to give 0.854 g (2.7 mmol) of the above-mentioned compound as white crystals.

$^1$H-NMR (300 MHz, CDCl$_3$) δ: 1.93–2.03 (m, 1H), 2.08–2.20 (m, 1H), 3.00 (dd, J=7. 1, 13.8 Hz, 1H), 3.10 (dd, J=6.8, 13.8 Hz, 1H), 3.75–3.92 (m, 4H), 3.98 (d, J=16.2 Hz, 1H), 4.16 (d, J=16.2 Hz, 1H), 4.75 (br.q, J=approx. 7.5 Hz, 1H), 5.17–5.22 (m, 1H), 5.36 (br.d, J=7.14 Hz, 1H), 5.15–5.21 (m, 1H), 7.20–7.34 (m, 5H)

$^{13}$C-NMR (75 MHz, CDCl$_3$) δ: 32.7, 37.7, 47.3, 58.5, 66.9, 73.1, 75.9, 127.5, 129.0, 129.0, 135.2, 155.4, 201.0

Example 27

Production of (2S,3S)-1-chloro-2-hydroxy-3-(N-(S)-tetrahydrofuran-3'-yloxycarbonyl)amino-4-phenylbutane (VId)

0.706 g (2.26 mmol) of (3S)-1-chloro-2-oxo-3-(N-(S)-tetrahydrofuran-3'-yloxycarbonyl)amino-4-phenylbutane (Vd) was dissolved in a mixed solvent containing 8 ml of dichloromethane and 80 ml of methanol. 60 mg (1.6 mmol) of sodium borohydride was added thereto at −3° C. for 5 minutes, and the mixture was further stirred for 60 minutes at −3° C. 0.385 ml (6.72 mmol) of acetic acid was added to the reaction mixture, and the mixture was concentrated under reduced pressure to remove methanol. 5 ml of water was added thereto, and the resulting mixture was extracted twice with dichloromethane (20 ml and 10 ml). The combined organic layer was concentrated to give the mixture of above-mentioned compound and the diastereomer ((2R,3S)-form) (at ratio of approximately 83:17) as white crystals.

(2S,3S) -form)

$^1$H-NMR (300 MHz, CDCl$_3$) δ: 1.90–2.00 (m, 1H), 2.05–2.18 (m, 1H), 2.80 (dd, J=9.3, 14.0 Hz, 1H), 3.01 (dd, J=4.3, 14.0 Hz, 1H), 3.54 (br.s, 1H), 3.52–3.66 (m, 2H), 3.67–3.90 (m, 5H), 3.94–4.03 (m, 1H), 5.08–5.16 (m, 1H), 5.64 (br.d, J=9.4 Hz, 1H), 7.20–7.30 (m, 5H)

$^{13}$C-NMR (75 MHz, CDCl$_3$) δ: 32.4, 35.1, 46.8, 54.2, 66.5, 72.9, 73.0, 74.7, 126.0, 128.0, 129.1, 137.6, 155.5

Mass spectrum (ESI) 314.3 (MH$^+$)

Example 28

Production of (2S,3S)-3-(N-(S)-tetrahydrofuran-3'-yl oxycarbonyl)amino-4-phenylbutane-1,2-epoxide (VIIc)

The crude diastereomeric mixture of (2S, 3S)-1-chloro-2-hydroxy-3-(N-(S)-tetrahydrofuran-3'-yloxycarbonyl) amino-4-phenylbutane (VId) obtained in Example 27 ((2S, 3S)-(VIb) and (2R,3S)-(VIb) at a ratio of 83:17) was dissolved in 20 ml of methanol. To this solution was added 624 mg (4.52 mmol) of potassium carbonate at room temperature, and the mixture was further stirred at room temperature for 2 hours for reaction. After the insoluble matter of the reaction mixture was removed by filtration, the filtrate was concentrated under reduced pressure below 35° C. The resulting mixture was acidified with 10 ml of 0.5 N hydrochloric acid and was extracted twice with dichloromethane (10 ml and 10 ml). The organic layer was concentrated at 40° C. to give 0.58 g (2.1 mmol) of the mixture of the above-mentioned compound and its diastereomer (2R,3S)-(VIIb) (at a ratio of 83:17) as white crystals.

(2S,3S) -form)

$^1$H-NMR (300 MHz, CDCl$_3$) δ: 2.72–2.78 (m, 2H), 2.78–2.83 (m, 1H), 2.86–3.02 (m, 2H), 3.70–3.90 (m, 5H), 4.65–4.68 (br., 1H), 5.15–5.21 (m, 1H), 7.20–7.34 (m, 5H)

$^{13}$C-NMR (75 MHz, CDCl$_3$) δ: 32.7, 37.5, 46.7, 53.0, 53.0, 66.9, 73.2, 75.4, 126.9, 128.7, 129.4, 136.3, 155.5

Mass spectrum (ESI) 278.2 (MH$^+$)

Example 29

Production of (2R,3S)-3-(N-(S)-tetrahvdrofuran-3'-yl oxycarbonyl amino-2-hydroxy-1-(N-isobutyl)amino-4-phenylbutane (IXd)

0.58 g (2.1 mmol) of the diastereomeric mixture of 3-(N-(S)-tetrahydrofuran-3'-yloxycarbonyl)amino-4-phenylbutane-1,2-epoxide (VIIc) obtained in Example 28 ((2S,3S)-(VIIc) and (2R,3S)-(VIIc) at a ratio of 83:17) was suspended in 4 ml of ethanol. To this suspension was added 3.4 ml (33.9 mmol) of isobutylamine, and the mixture was stirred at 70° C. for 1 hour for reaction. The reaction solution was concentrated to give the mixture of the above-mentioned compound and its diastereomer (2S,3S)-(VIIIa) (at a ratio of 83:17) as white crystals.
(2R,3S) -form)

$^1$H-NMR (300 MHz, CDCl$_3$) δ: 0.91 (d, J=6.6 Hz, 6H), 1.72 (hep, J=6.6 Hz, 1H), 1.80–1.95 (m, 1H), 2.02–2.14 (m, 1H), 2.37–2.44 (m, 2H), 2.64–2.99 (m, SH), 3.55–3.86 (m, SH), 5.11 (br., 1H), 5.43 (br.d, J=8.7 Hz, 1H), 7.19–7.28 (m, 5H)

$^{13}$C-NMR (75 MHz, CDCl$_3$) δ: 20.4, 28.2, 32.7, 36.6, 51.4, 55.2, 57.7, 66.8, 70.3, 73.2, 75.0, 126.3, 128.3, 129.3, 137.7, 155.9 Mass spectrum (ESI) 351.3 (MH$^+$)

Example 30

Production of 4-Nitro-N-((2'R(svn),3'S)-2'-hydroxy-4'-phenyl-3'-(N-(S)-tetrahydrofuran-3"-yloxycarbonyl)amino-butyl)-N-isobutyl-benzenesulfonamide (IXe)

The diastereomeric mixture of (2R,3S)-3-(N-(S)-tetrahydrofuran-3'-yloxycarbonyl)amino-2-hydroxy-1-(N-isobutyl)amino-4-phenylbutane (IXd) obtained in Example 29 ((2R,3S)-(IXd) and (2S,3S)-(IXd) at a ratio of 83:17) was dissolved in 2 ml of dichloromethane. To this solution was added 0.233 g (2.2 mmol) of sodium carbonate dissolved in 2 ml of water, and 0.488 g (2.2 mmol) of 4-nitrobenzenesulfonylchloride dissolved in 1 ml of dichloromethane was added thereto with ice cooling for 2 minutes. While the reaction mixture was further stirred for 3 hours at room temperature, 6 ml of dichloromethane and 2 ml of water were added thereto because it was difficult to stir the mixture owing to deposition of the crystals. The organic layer was separated and the resulting organic layer was concentrated to give 0.974 g of the mixture of the above-mentioned compound and its diastereomer (2'S,3'S)-(IXe) (at a ratio of 83:17) as white crystals.

These crude crystals were dissolved in 60 ml of ethanol at 70° C. After the crystallization was started at 55° C., it was cooled to 5° C. The resulting crystals were filtered and washed with 5 ml of ethanol. The crystals obtained were dried under reduced pressure to give 0.642 g (96.4% de) of the above-mentioned compound.

This crystals was recrystallized from 50 ml of ethanol to give 0.583 g of the above-mentioned compound (100% de). ((2'R(syn),3'S) -form)

$^1$H-NMR (300 MHz, CDCl$_3$) δ: 0.87 (d, J=7.0 Hz, 3H), 0.89 (d, J=7.0 Hz, 3H), 1.89 (hep, J=6.8, 1H), 1.90–1.94 (m, 1H), 2.08–2.15 (m, 1H), 2.86–3.04 (m, 4H), 3.11–3.24 (m, 2H), 3.58 (br.s, 6H), 3.65–3.87 (m, 6H), 4.85 (br.d, J=5.2 Hz, 1H), 5.10–5.18 (m, 1H), 7.20–7.37 (m, 5H), 7.95 (d, J=8.9 Hz, 2H), 8.34 (d, J=8.9 Hz, 2H)

$^{13}$C-NMR (75 MHz, CDCl$_3$) δ: 19.8, 19.9, 27.0, 32.7, 35.4, 52.7, 55.3, 57.8, 66.8, 72.1, 73.1, 75.6, 124.3, 126.7, 128.5, 128.6, 129.3, 137.2, 144.7, 150.0, 156.2 Mass spectrum (FAB) 536 (MH$^+$)

Example 31

Production of (4R)-4-(N-benzyloxycarbonyl)amino-3-oxo-5-phenylthiopentanoic acid tert-butyl ester (IIf)

A solution (2.0M) (420 ml, 840 mmol) of LDA in heptane, THF and ethylbenzene was dissolved in 800 ml of anhydrous THF under an argon atmosphere, and the mixed solution was cooled to –66° C. To this solution was added dropwise a solution of 99.54 g (856.9 mmol) of tert-butyl acetate in 53 ml of THF over approximately 10 minutes while maintaining the temperature at –69° C. to –71° C. After the completion of the dropwise addition, the mixture was stirred at –69° C. to –74° C. for 60 minutes. To this solution was added dropwise a solution of 80.00 g (231.6 mmol) of N-benzyloxycarbonyl-(S-phenyl)-L-cysteine methyl ester (If) in 135 ml of THF over approximately 45 minutes while maintaining the temperature at –69° C. to –73° C. After the completion of the dropwise addition, the reaction solution was stirred at –69° C. to –74° C. for 2.5 hours. The reaction solution was added to 150 ml of 36% hydrochloric acid dissolved in 750 ml of water. To this was added 80 ml of ethyl acetate, and the organic layer was separated. The resulting water layer was extracted with 550 ml of ethyl acetate. The organic layers were combined and were washed with 300 ml of 1 N hydrochloric acid, saturated sodium hydrogencarbonate aqueous solution and saturated sodium chloride aqueous solution in that order. The organic layer was dried over anhydrous sodium sulfate, and the filtrate was concentrated to give 108.04 g (79.9 wt %, 86.33 g) of the above-mentioned crude compound. The yield was 86.8%.

$^1$H-NMR (300 MHz, CDCl$_3$) δ: 3.28 (dd, 1H), 3.36–3.52 (m, 3H), 4.60 (dd, 1H), 5.07 (d, 1H), 5.10 (d, 1H), 5.58 (br.d, 1H), 7.19–7.40 (m, 1OH). Mass spectrum (ESI) 452 (MNa$^+$)

Example 32

Production of (3R)-3-(N-benzyloxycarbonyl)amino-1-chloro-2-oxo-4-phenylthiobutane (Ve)

108.04 g (79.9 wt %, 86.33 g, 201.0 mmol) of (4R)-4-(N-benzyloxycarbonyl)amino-3-oxo-5-phenylthiopentanoic acid tert-butyl ester (IIf) was dissolved in 320 ml of dichloromethane, and was cooled to –32° C. 34.38 g (254.7 mmol) of sulfuryl chloride dissolved in 22 ml of dichloromethane was added dropwise thereto over 80 minutes while being stirred at –32° C. to –31° C., and the mixture was further stirred for 80 minutes at –32° C. to –31° C. To the reaction mixture was added 300 ml of water, and the organic layer was separated. The resulting organic layer was washed with saturated sodium hydrgencarbonate aqueous solution and saturated sodium chloride aqueous solution in that order, and was dried over sodium sulfate. The filtrate was concentrated, and the resulting residue was dissolved in 192 ml of formic acid (90%), and the mixture was stirred for 4 hours at 50° C. to 52° C. This reaction mixture was concentrated under reduced pressure, and to the resulting mixture was added 200 ml of 2-propanol. The mixture was concentrated again, and to the resulting mixture was added 400 ml of 2-propanol to form the crystals. The crystals formed were dissolved at 52° C., and the solution was cooled to 5° C. The resulting crystals were collected by filtration and were washed with 150 ml of 2-propanol to give 51.5 g (98.0 wt %, 50.47 g) of the above-mentioned compound as white crystals. The yield was 59.9%.

$^1$H-NMR (300 MHz, CDCl$_3$) δ: 3.32 (dd, 1H), 3.42 (dd, 1H), 4.13 (d, 1H), 4.72 (d, 1H), 4.73 (dd, 1H), 5.00 (s, 2H) 5.57 (br.d, 1H), 7.22–7.40 (m, 1OH). Mass spectrum (ESI) 364 (MH$^+$)

Example 33

Production of (2R,3S) -3-(N-benzyloxycarbonyl)amino-1-chloro-2-hydroxy-4-phenylthiobutane (VIe)

51.5 g (98.0 wt %, 50.47 g, 138.7 mmol) of (3R)-3-(N-benzyloxycarbonyl)amino-1-chloro-2-oxo-4-phenylthiobutane (Ve) was dissolved in a mixed solvent containing 300 ml of dichloromethane and 187 ml of methanol. 3.64 g (96.2 mmol) of sodium borohydride was added portionwise thereto at –11° C. to –9° C. over 1 hour, and the mixture was further stirred for 40 minutes at –12° C. to –9°

C. 48 ml of 2 N hydrochloric acid was added to the reaction mixture, and the mixture was concentrated under reduced pressure to remove methanol. 500 ml of dichloromethane and 300 ml of water were added thereto, and the organic layer was separated. The resulting organic layer was washed with 300 ml of saturated sodium chloride aqueous solution and was dried over sodium sulfate. The filtrate was concentrated to give the mixture of above-mentioned compound and the diastereomer ((2R,3S)-form) (at a ratio of approximately 83:17) as the result of the HPLC analysis.

The crude crystals were dissolved in 200 ml of ethyl acetate and 300 ml of hexane at 60° C. The solution was cooled to 5° C, and the resulting crystals were collected by filtration and were washed with 170 ml of a mixed solvent containing hexane and ethyl acetate at a ratio of 2:1 to give 38.77 g (98.6% de) of the above-mentioned compound as white crystals. The yield was 76.4%.
((2R,3S) -form)
$^1$H-NMR, (300 MHz, CDCl$_3$) δ: 3.29 (d, 2H), 3.60 (dd, 1H) 3.68 (dd, 1H), 3.88–3.96 (m, 2H), 5.07 (s, 2H), 5.15 (br., 2H), 7.18–7.39 (m, 10H)

Example 34

Production of (3S)-3-(N-benzyloxycarbonyl)amino-3-benzyl-2-oxo-1-chloropropane (Vb)

1.00 g (2.38 mmol) of N-benzyloxycarbonyl-L-phenylalanine p-nitrophenyl ester (Ig) and 1.45 ml (9.38 mmol) of trimethylsilyl chloroacetate (IVb) were dissolved in 10 ml of THF under an argon atmosphere, and the mixed solution was cooled to −75° C. To this solution was added dropwise a solution (2.0M) (4.52 ml, 9.04 mmol) of LDA in heptane, THF, and ethylbenzene as dissolved in 4 ml of anhydrous THF over approximately 1 hour and 15 minutes while maintaining the temperature at −72° C. to −65° C. After the completion of the dropwise addition, the mixture was stirred at −72° C for 3 hours. 20 ml of 10% citric acid aqueous solution was added to the reaction solution to stop the reaction. The temperature was then raised to room temperature, and 20 ml of ethyl acetate was added. The resulting organic layer was separated and was washed with 10 ml of water twice. The organic layer was dried over anhydrous magnesium sulfate, and the filtrate was concentrated to give the above-mentioned crude compound. As the result of HPLC analysis, this crude compound contained 316.6 mg (0.954 mmol, 48.4%) of the above-mentioned compound (Vb) and the starting material N-benzyloxycarbonyl-L-phenylalanine p-nitrophenyl ester (Ig) 398.8 mg (0.949 mmol, 39.9%).

Example 35

Production of (3S)-3-(N-tert-butyloxycarbonyl)amino-3-benzyl-2-oxo-1-chloro-propane (Vf)

1.002 g (2.594 mmol) of N-tert-butyloxycarbonyl-L-phenylalanine p-nitrophenyl ester (Ih) and 2.04 ml (12.96 mmol) of trimethylsilyl chloroacetate (IVb) were dissolved in 10 ml of THF under an argon atmosphere, and the mixed solution was cooled to −70° C. To this solution was added dropwise a solution (2.0M) (6.47 ml, 12.95 mmol) of LDA in heptane, THF and ethylbenzene as dissolved in 9 ml of anhydrous THF over approximately 70 minutes while maintaining the temperature at −70° C. to −68° C. After the completion of the dropwise addition, the mixture was stirred at −70° C. for 3 hours. 20 ml of 10 citric acid aqueous solution was added to the reaction solution to stop the reaction. The temperature was then raised to room temperature, and 20 ml of ethyl acetate was added. The resulting organic layer was separated and was washed with 10 ml of water twice. The organic layer was dried over anhydrous magnesium sulfate, and the filtrate was concentrated to give the above-mentioned crude compound. As the result of HPLC analysis, this crude compound contained 413.5 mg (1.389 mmol, 53.5%) of the above-mentioned compound (Vf) and the starting material N-tertbutyloxycarbonyl-L-phenylalanine p-nitrophenyl ester (Ih) 164 mg (0.425 mmol, 16.4%).

Example 36

Production of (3S)-3-(N-tert-butyloxycarbonyl)amino-3-benzyl-2-oxo-1-chloropropane (Vf)

A solution (2.0 M) 14.9 ml, 9.8 mmol) of LDA in heptane, THF and ethylbenzene was dissolved 1in 10 ml of anhydrous THF under an argon atmosphere, and the mixed solution was cooled to −75° C. To this solution was added dropwise a solution of 463 mg (4.9 mmol) of chloroacetic acid (IVc) in 3.5 ml of THF over approximately 20 minutes while maintaining the temperature at −75° C. to −70° C. After the completion of the dropwise addition, the mixture was stirred at −75° C. to −70° C. for 30 minutes. To this solution was added dropwise a solution of 500 mg (1.29 mmol) of N-tert-butyloxycarbonyl-L-phenylalanine p-nitrophenyl ester (Ih) in 4 ml of THF over approximately 15 minutes while maintaining the temperature of −75° C. to −70° C. After the completion of the dropwise addition, the reaction solution was stirred at −75° C. to −70° C. for 3 hours, and 20 ml of 10% citric acid aqueous solution was added to the reaction solution to stop the reaction. The temperature was then raised to room temperature, and 20 ml of ethyl acetate was added, and the resulting organic layer was separated. The organic layer was washed with 20 ml of saturated sodium hydrogencarbonate aqueous solution and 20 ml of saturated sodium chloride aqueous solution in that order. The organic layer was dried over anhydrous sodium sulfate, and the filtrate was concentrated to give the above-mentioned crude compound. As the result of HPLC analysis, this crude compound contained 186 mg (0.625 mmol) of the above-mentioned compound (Vf). The yield was 48.4%.

For convenience, the compounds which were used or synthesized in the above-mentioned Production Examples and Examples are shown below.

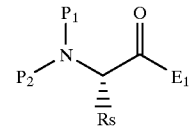

(Ia)  Rs = P$_1$ = P$_2$ = E$_1$ = OBn
(Ib)  Rs = P$_1$ = P$_2$ = Bn, E$_1$ = OPNP
(Ic)  Rs = Bn, P$_1$ = Z, P$_2$ = H, E$_1$ = OMe
(Id)  Rs = Bn, P$_1$ = Boc, P$_2$ = H, E$_1$ = OMe

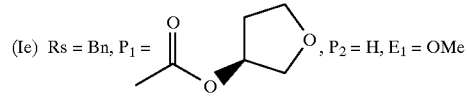

(If)  Rs = CH$_2$SPh, P$_1$ = Z, P$_2$ = H, E$_1$ = OMe
(Ig)  Rs = Bn, P$_1$ = Z, P$_2$ = H, E$_1$ = OPNP
(Ih)  Rs = Bn, P$_1$ = Boc, P$_2$ = H, E$_1$ = OPNP

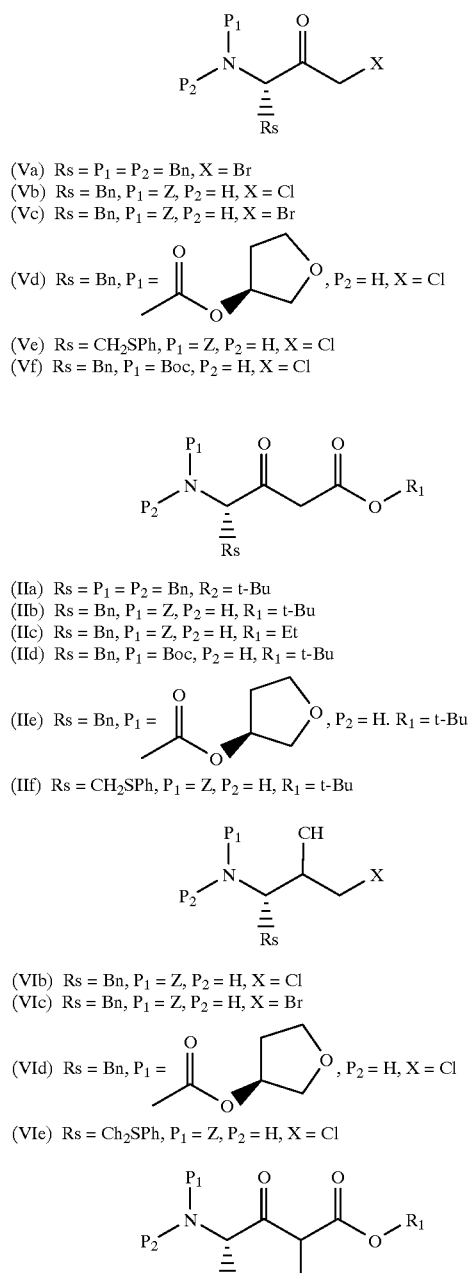

(Va) Rs = P₁ = P₂ = Bn, X = Br
(Vb) Rs = Bn, P₁ = Z, P₂ = H, X = Cl
(Vc) Rs = Bn, P₁ = Z, P₂ = H, X = Br (Vd) Rs = Bn, P₁ = [acetoxy-tetrahydrofuranyl], P₂ = H, X = Cl (Ve) Rs = CH₂SPh, P₁ = Z, P₂ = H, X = Cl
(Vf) Rs = Bn, P₁ = Boc, P₂ = H, X = Cl (IIa) Rs = P₁ = P₂ = Bn, R₂ = t-Bu
(IIb) Rs = Bn, P₁ = Z, P₂ = H, R₁ = t-Bu
(IIc) Rs = Bn, P₁ = Z, P₂ = H, R₁ = Et
(IId) Rs = Bn, P₁ = Boc, P₂ = H, R₁ = t-Bu (IIe) Rs = Bn, P₁ = [acetoxy-tetrahydrofuranyl], P₂ = H, R₁ = t-Bu (IIf) Rs = CH₂SPh, P₁ = Z, P₂ = H, R₁ = t-Bu (VIb) Rs = Bn, P₁ = Z, P₂ = H, X = Cl
(VIc) Rs = Bn, P₁ = Z, P₂ = H, X = Br (VId) Rs = Bn, P₁ = [acetoxy-tetrahydrofuranyl], P₂ = H, X = Cl (VIe) Rs = Ch₂SPh, P₁ = Z, P₂ = H, X = Cl (IIIa) Rs = P₁ = P₂ = Bn, R₁ = t-Bu, X = Br
(IIIb) Rs = Bn, P₁ = Z, P₂ = H, R₁ = t-Bu, X = Cl
(IIIc) Rs = Bn, P₁ = Z, P₂ = H, R₁ = t-Bu, X = Br
(IIId) Rs = P₁ = P₂ = Bn, R₁ = t-Bu, X = Cl (IIIe) Rs = Bn, P₁ = [acetoxy-tetrahydrofuranyl], P₂ = H, R₁ = t-Bu, X = Cl

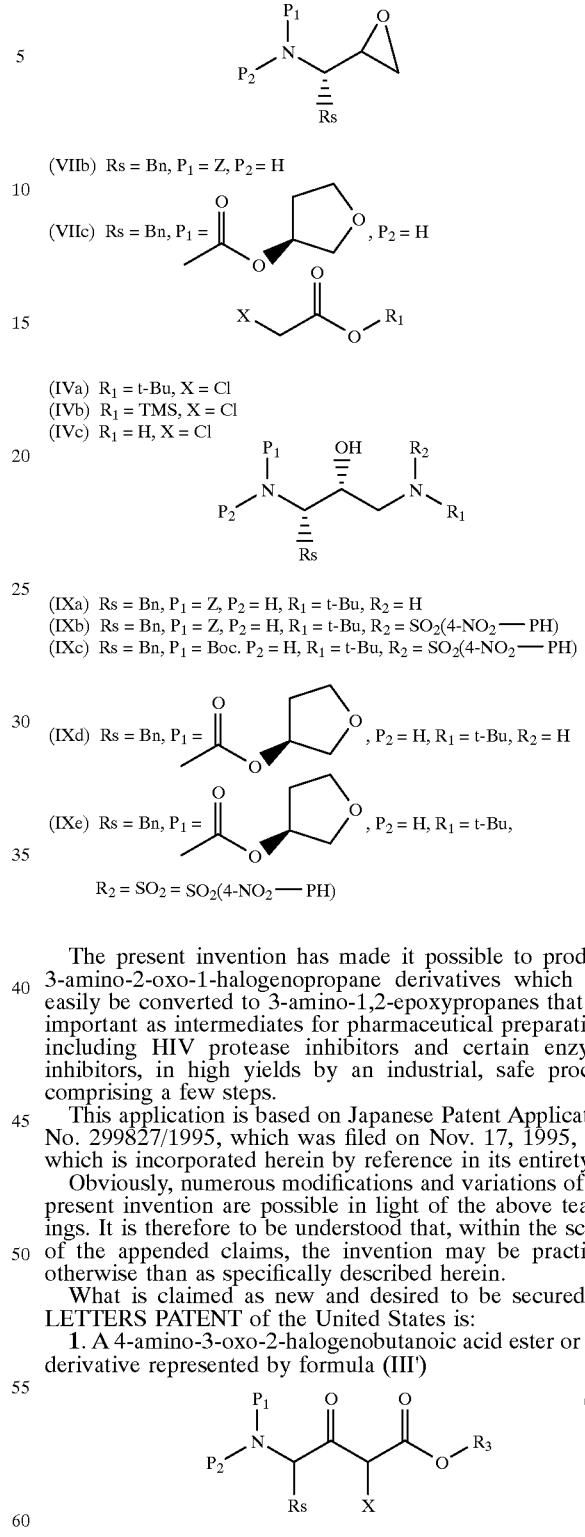

(VIIb) Rs = Bn, P₁ = Z, P₂ = H (VIIc) Rs = Bn, P₁ = [acetoxy-tetrahydrofuranyl], P₂ = H (IVa) R₁ = t-Bu, X = Cl
(IVb) R₁ = TMS, X = Cl
(IVc) R₁ = H, X = Cl (IXa) Rs = Bn, P₁ = Z, P₂ = H, R₁ = t-Bu, R₂ = H
(IXb) Rs = Bn, P₁ = Z, P₂ = H, R₁ = t-Bu, R₂ = SO₂(4-NO₂—PH)
(IXc) Rs = Bn, P₁ = Boc. P₂ = H, R₁ = t-Bu, R₂ = SO₂(4-NO₂—PH)

(IXd) Rs = Bn, P₁ = [acetoxy-tetrahydrofuranyl], P₂ = H, R₁ = t-Bu, R₂ = H (IXe) Rs = Bn, P₁ = [acetoxy-tetrahydrofuranyl], P₂ = H, R₁ = t-Bu,

R₂ = SO₂ = SO₂(4-NO₂—PH)

The present invention has made it possible to produce 3-amino-2-oxo-1-halogenopropane derivatives which can easily be converted to 3-amino-1,2-epoxypropanes that are important as intermediates for pharmaceutical preparations including HIV protease inhibitors and certain enzyme inhibitors, in high yields by an industrial, safe process comprising a few steps.

This application is based on Japanese Patent Application No. 299827/1995, which was filed on Nov. 17, 1995, and which is incorporated herein by reference in its entirety.

Obviously, numerous modifications and variations of the present invention are possible in light of the above teachings. It is therefore to be understood that, within the scope of the appended claims, the invention may be practiced otherwise than as specifically described herein.

What is claimed as new and desired to be secured by LETTERS PATENT of the United States is:

1. A 4-amino-3-oxo-2-halogenobutanoic acid ester or salt derivative represented by formula (III')

(III')

wherein

R$_s$ represents hydrogen, an optionally substituted alkyl group having from 1 to 10 carbon atoms, an optionally substituted aryl group having from 6 to 15 carbon atoms, an optionally substituted aralkyl group having from 7 to 20 carbon atoms, or the above-mentioned groups containing a hetero atom in the carbon skeleton; P$_1$ and P$_2$, independently from each other, represent hydrogen or an amino-protecting group, or P$_1$ and P$_2$, together form a difunctional amino-protecting group, and at least one of P$_1$ and P$_2$ is not hydrogen; R$_3$ represents an alkali metal, an optionally substituted alkyl group having from 1 to 10 carbon atoms, an optionally substituted aryl group having from 6 to 15 carbon atoms, an optionally substituted aralkyl group having from 7 to 20 carbon atoms, a trialkylsilyl group having from 3 to 10 carbon atoms, a phenyldialkylsilyl group having 8 to 10 carbon atoms or a diphenylalkylsilyl group having 13 to 15 carbon atoms;

and X represents a halogen atom other than fluorine, or its salt.

2. The compound or salt of claim 1, wherein the carbon atom to which R$_s$ is bonded has an S-configuration except for a case where R$_s$ in formula (III') is hydrogen.

3. The compound or salt of claim 1, wherein the carbon atom to which R$_s$ is bonded has an R-configuration except for a case where R$_s$ in formula (III') is hydrogen.

* * * * *